United States Patent
Augustine et al.

[11] Patent Number: 6,013,097
[45] Date of Patent: *Jan. 11, 2000

[54] WOUND TREATMENT DEVICE FOR ATTACHMENT TO SKIN

[75] Inventors: Scott D. Augustine, Bloomington; Randall C. Arnold, Minnetonka; Donald E. Stapf, Minnesota; Gregory P. Hamlin, St. Paul, all of Minn.

[73] Assignee: Augautine Medical, Inc., Eden Prairie, Minn.

[ * ] Notice: This patent is subject to a terminal disclaimer.

[21] Appl. No.: 08/836,066

[22] PCT Filed: Nov. 21, 1995

[86] PCT No.: PCT/US95/15197
§ 371 Date: Apr. 29, 1997
§ 102(e) Date: Apr. 29, 1997

[87] PCT Pub. No.: WO96/15745
PCT Pub. Date: May 30, 1996

Related U.S. Application Data

[63] Continuation-in-part of application No. 08/342,741, Nov. 21, 1994.

[51] Int. Cl.⁷ .............................................. A61F 7/00
[52] U.S. Cl. .............................. 607/96; 607/114; 602/2; 602/14
[58] Field of Search .............................. 607/96, 108, 112; 602/2, 14

[56] References Cited

U.S. PATENT DOCUMENTS

| | | |
|---|---|---|
| 222,690 | 12/1879 | Goldschmidt . |
| 697,637 | 4/1902 | Lee . |
| 720,812 | 2/1903 | Johnson . |
| 1,384,467 | 7/1921 | Homan . |
| 1,399,095 | 12/1921 | Webb, Sr. . |
| 1,777,982 | 10/1930 | Popp . |
| 1,920,808 | 8/1933 | Sander ................................ 128/154 |
| 1,979,082 | 10/1934 | Schwedenberg et al. ............ 219/46 |
| 2,221,758 | 11/1940 | Elmquist ................................ 128/154 |
| 2,443,481 | 6/1948 | Sene ...................................... 128/155 |
| 2,573,791 | 11/1951 | Howells ................................ 128/82.1 |
| 2,577,945 | 12/1951 | Atherton .............................. 128/156 |
| 2,599,523 | 6/1952 | Dorr ...................................... 128/153 |
| 2,601,189 | 6/1952 | Wales, Jr. .............................. 4/160 |
| 2,632,443 | 3/1953 | Lesher .................................. 128/156 |
| 2,706,988 | 4/1955 | Weber .................................. 128/102 |
| 2,769,892 | 11/1956 | Collins .................................. 219/46 |
| 3,026,874 | 3/1962 | Stevens ................................ 128/260 |
| 3,528,416 | 9/1970 | Chamberlain ...................... 128/154 |
| 3,596,657 | 8/1971 | Eidus .................................. 128/156 |
| 3,610,238 | 10/1971 | Rich, Jr. .............................. 128/184 |
| 3,610,251 | 10/1971 | Sanderson .......................... 128/379 |

(List continued on next page.)

FOREIGN PATENT DOCUMENTS

| | | |
|---|---|---|
| 0 424 165 | 4/1991 | European Pat. Off. . |
| 0 485 657 | 5/1992 | European Pat. Off. . |
| 0 607 472 A1 | 7/1994 | European Pat. Off. . |
| 1 303 238 | 7/1962 | France . |
| 1 489 127 | 7/1967 | France . |
| 1 527 887 | 6/1968 | France . |
| 2 544 202 | 10/1984 | France . |
| 31 02 674 | 9/1982 | Germany . |
| 31 18 232 | 11/1982 | Germany . |
| 35 39 533 | 5/1987 | Germany . |
| 269 938 | 7/1950 | Switzerland . |
| 378 465 | 7/1964 | Switzerland . |
| 3090 | 6/1902 | United Kingdom . |
| 288 220 | 7/1927 | United Kingdom . |
| 2 082 919 | 3/1982 | United Kingdom . |
| 2 199 501 | 7/1988 | United Kingdom . |
| 2 261 822 | 6/1993 | United Kingdom . |
| WO 89/04158 | 5/1989 | WIPO . |
| WO 94/00090 | 6/1994 | WIPO . |
| WO 96 15745 | 5/1996 | WIPO . |

Primary Examiner—Robert L. Nasser
Attorney, Agent, or Firm—Gray Cary Ware Freidenrich

[57] ABSTRACT

A non-contact wound treatment device having a flexible portion to accommodate patient motion without peeling off. A removable wound heater may be used to treat the wound area.

46 Claims, 18 Drawing Sheets

6,013,097
Page 2

U.S. PATENT DOCUMENTS

| | | | |
|---|---|---|---|
| 3,687,143 | 8/1972 | Schneeberger et al. | 128/402 |
| 3,691,646 | 9/1972 | Ruffolo | 34/90 |
| 3,782,377 | 1/1974 | Rychlik | 128/132 |
| 3,814,095 | 6/1974 | Lubens | 128/260 |
| 3,867,939 | 2/1975 | Moore | 128/254 |
| 3,881,477 | 5/1975 | Von Otto | 128/132 |
| 4,080,971 | 3/1978 | Leeper | 128/383 |
| 4,134,399 | 1/1979 | Halderson | 128/132 |
| 4,172,495 | 10/1979 | Zebuhr et al. | 165/46 |
| 4,279,255 | 7/1981 | Hoffman | 128/402 |
| 4,341,209 | 7/1982 | Schaar | 128/156 |
| 4,382,441 | 5/1983 | Svedman | 604/291 |
| 4,399,816 | 8/1983 | Spangler | 128/154 |
| 4,484,574 | 11/1984 | DeRusha et al. | 128/156 |
| 4,517,972 | 5/1985 | Finch, Jr. | 128/156 |
| 4,540,412 | 9/1985 | Van Overloop | 604/291 |
| 4,572,188 | 2/1986 | Augustine et al. | 128/380 |
| 4,628,930 | 12/1986 | Williams | 128/379 |
| 4,633,863 | 1/1987 | Filips et al. | 128/165 |
| 4,641,641 | 2/1987 | Strock | 128/132 |
| 4,641,643 | 2/1987 | Greer | 128/156 |
| 4,667,666 | 5/1987 | Fryslie | 128/156 |
| 4,890,608 | 1/1990 | Steer | 128/156 |
| 4,962,761 | 10/1990 | Golden | 128/400 |
| 4,969,881 | 11/1990 | Viesturs | 604/305 |
| 5,003,971 | 4/1991 | Buckley | 128/156 |
| 5,025,777 | 6/1991 | Hardwick | 126/263 |
| 5,060,662 | 10/1991 | Farnswoth, III | 128/888 |
| 5,086,763 | 2/1992 | Hathman | 602/42 |
| 5,107,832 | 4/1992 | Guibert et al. | 128/399 |
| 5,135,518 | 8/1992 | Vera | 604/291 |
| 5,144,113 | 9/1992 | Hall et al. | 219/549 |
| 5,144,958 | 9/1992 | Krueger et al. | 128/743 |
| 5,170,781 | 12/1992 | Loomis | 128/118.1 |
| 5,190,031 | 3/1993 | Guibert et al. | 128/399 |
| 5,230,350 | 7/1993 | Fentress | 128/846 |
| 5,431,622 | 7/1995 | Pyrozyk et al. | 602/2 |
| 5,531,670 | 7/1996 | Westby et al. | 602/41 |
| 5,609,619 | 3/1997 | Pompei | 607/104 |
| 5,649,972 | 7/1997 | Hochstein | 607/100 |

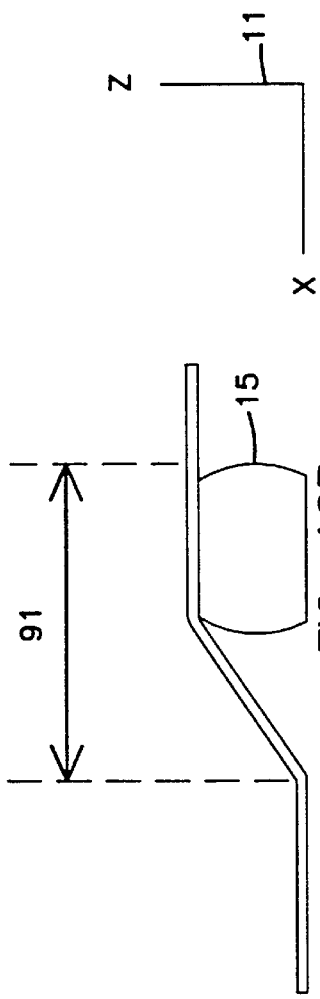
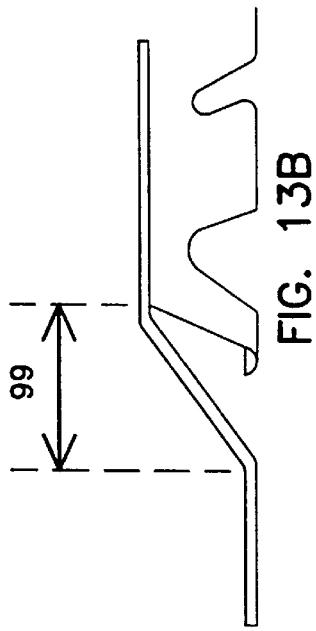
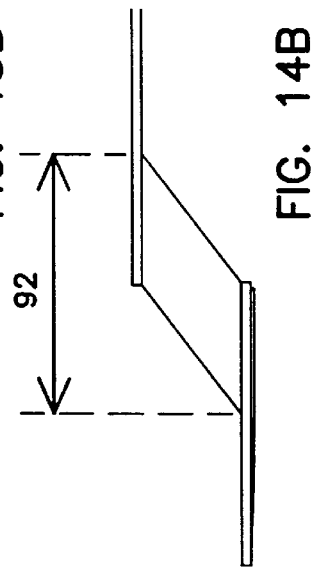
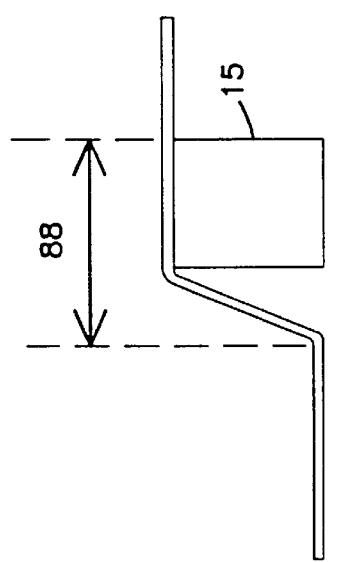
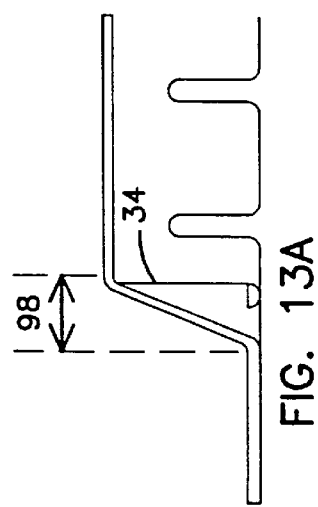
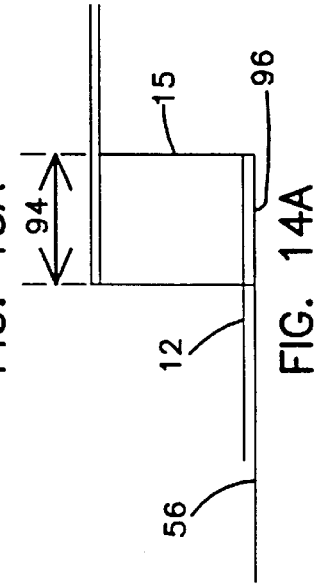

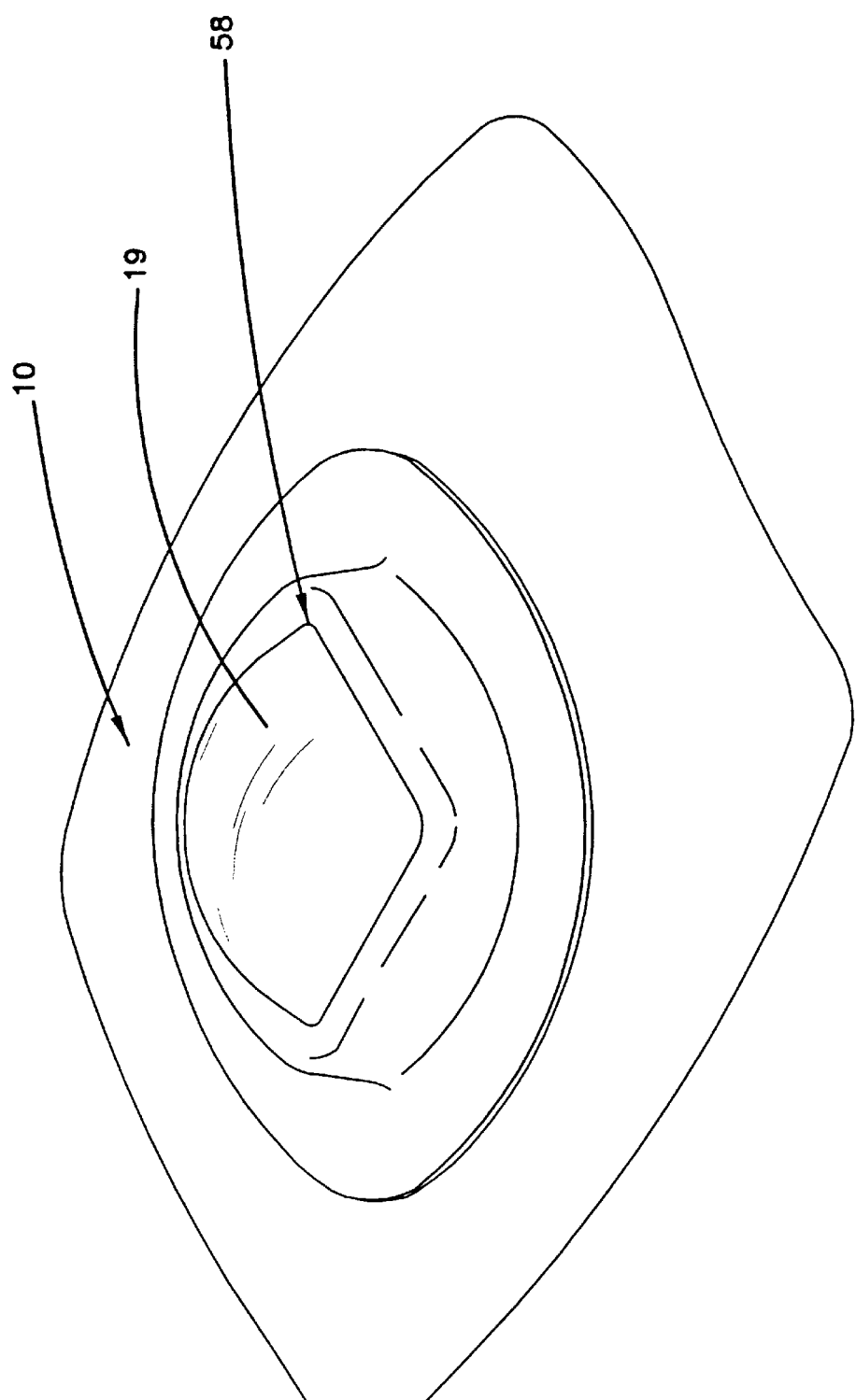

WOUND TREATMENT DEVICE FOR ATTACHMENT TO SKIN

CROSS REFERENCE TO RELATED CASES

For the United States National Stage Application, this application is a Continuation-in-Part of U.S. Ser. No. 08/342,741, filed Nov. 21, 1994 assigned commonly with this application.

This application contains material related to the following pending U.S. patent applications all assigned commonly with this application:

- U.S. Ser. No. 07/900,656 filed Jun. 19, 1992, for THERMAL BODY TREATMENT APPARATUS AND METHOD;
- U.S. Ser. No. 08/342,741, filed Nov. 21, 1994, for WOUND TREATMENT DEVICE;
- U.S. Ser. No. 08/356,325, filed Feb. 21, 1995, for WOUND COVERING;
- U.S. Ser. No. 08/785,794, filed Jan. 21, 1997, entitled NORMOTHERMIC HEATER WOUND COVERING;
- U.S. Ser. No. 08/786,714, filed Jan. 21, 1997, for NEAR HYPERTHERMIC HEATER WOUND COVERING;
- U.S. Ser. No. 08/786,713, filed Jan. 21, 1997, for NORMOTHERMIC TISSUE HEATING WOUND COVERING;
- U.S. Ser. No. 08/838,618, filed Apr. 11, 1997, for FLEXIBLE NON-CONTACT WOUND TREATMENT DEVICE; and
- U.S. Ser. No. 08/842,073, filed Apr. 11, 1997, for FLEXIBLE NON-CONTACT WOUND TREATMENT DEVICE WITH A SINGLE JOINT

TECHNICAL FIELD

The invention relates to a wound treatment device for covering and in some applications heating skin lesions, surgical wounds and the like.

The wound treatment device includes a wound cover and optionally a detachable wound heater which provide a non-contact wound treatment volume over the wound area.

The invention also relates to methods for making and using the wound treatment device.

BACKGROUND OF THE INVENTION

One traditional method of treating a wound involves the placement of a sterile gauze over the wound area and holding the gauze in place with an adhesive tape. This type of wound dressing has numerous shortcomings. The wound is not fully isolated from the air and can exchange bacteria with the environment. The gauze can adhere to the wound itself interfering with the healing process which is undesirable. This traditional form of bandage does not control the thermal environment of the wound which is also undesirable.

Although some forms of wound heaters and non-contact wound coverings are known from Veilhan Fr. 1,527,887 (1969) they are not generally accepted for several reasons. For example, wound coverings which include a rigid enclosure forming a cavity that covers the wound are usually adhesively attached to the skin of the patient with a relatively inelastic material. As a result the wound covering is unable to accommodate patient motion. Consequently patient motion will cause the rigid wound covering to "peel-off" of the patient's skin. The traditional solution to this problem has been to use a more aggressive adhesive tape or the like to more firmly attach the wound covering to the skin. This solution to the problem results in an uncomfortable bandage.

The traditional wound covering does not permit close control over the temperature of the wound area. Prior art heated bandages which rely on a non-contact enclosure may use point source type heaters which result in variations in radiant heat flux depending on the location of the heater within the enclosure. Therefore there is a need for a non-contact bandage which can be used to control the environment of the wound and which may be reliably and comfortably attached to the skin.

French Patent No. 1,527,887 issued to Veilhan discloses a rigid wound cover that sits directly on a patient's skin. Additionally, there is disclosed a heating element placed at the peripheral edge of the cover away from the wound. Rigidity is imposed on the Veilhan cover as a matter of necessity to provide structural support to the heater and other fixtures such as a light.

PCT International Application PCT/IT88/00006, International Publication No. WO 89/04158 to Checconi, et al., discloses a wound dressing using a rigid spacer between the plaster and the patient's skin. The plaster and the spacer are intended to provide for considerable aeration while avoiding any contact with the patient's wound. The Checconi device does not contemplate a need for deformability and stretchablility to accommodate patient motion.

PCT International Application PCT/US93/05876, International Publication No. WO 94/00090 to Augustine discloses a wound covering that, like Checconi, does not comprehend well the need to accommodate patient motion.

SUMMARY OF THE INVENTION

The wound treatment device 10 of the present invention has an upper wound covering surface displaced above the patient's skin surface, and an attachment surface lying generally in the plane of the patient's skin. Together these two surfaces define an enclosed non-contact volume over the wound treatment site.

The wound treatment device 10 may be divided into three separate parts for the purpose of description. These parts are an attachment portion 12, a wound treatment portion 14, and a transition portion 16. Each portion is designed to serve a separate function.

The attachment portion 12 is used to connect the wound treatment device 10 to the skin of a patient. The attachment portion 12 will usually be formed as an annular attachment rim. An adhesive will typically be placed on the attachment rim to couple the wound treatment device 10 to the patient. The attachment portion 12 lies near the patient's skin and defines a so called first plane.

The wound treatment portion 14 of the wound treatment device 10 is illustratively an assembly which includes a standoff 15 which rises above the patient's skin surface, and a wound cover 20 which spans the open portion of the standoff 15. The standoff 15 helps to define the vertical extent or dimension of the wound treatment device 10 and helps to define the location of a second plane which is used to describe the geometry of the device. Thus the wound treatment portion 14 includes a standoff 15 and a wound cover 20 which together define both a wound treatment volume 24 and a wound treatment area 26.

The wound treatment volume 24 is located over the surface of the wound. The atmosphere in this wound treatment volume 24 can be controlled by the wound treatment device 10.

In use the wound treatment area 26 is defined on the patient surface 18 under the wound treatment portion 14, and will typically be centered over the lesion or wound.

The transition portion 16 connects the attachment portion 12 to the wound treatment portion 14. This transition portion 16 improves the comfort and utility of the wound treatment device when the patient moves and stretches the wound treatment device 10. This stretching causes the total projected area of the wound treatment device 10 to increase and the shape of the wound treatment device 10 to change. In practice, the bulk of the patient motion is accommodated by the compliance of the transition portion 16. As a consequence, the transition portion projected area 17 increases. The standoff of wound treatment portion 14 rests gently on the patient's skin and it may twist to accommodate patient motion thus producing a device which conforms to the contour of the patient's body. However since the standoff can slide along the patient's skin there is no substantial change in the projected wound treatment area 28 due to patient motion. During patient motion the attachment portion 12 remains affixed to the surface of the patient and is easily deformed by body motion because of its relatively small area. Consequently the attachment portion projected area 40 may undergo a slight increase in area as the attachment portion 12 moves with the underlying skin. Throughout this motion the second shaped surface is supported above the patient's skin surface and can be used to support a detachable heater 32 which can heat the wound surface. A switch may also be provided to reduce power supplied to the wound treatment device 10 if the device is crushed in to contact with the wound.

BRIEF DESCRIPTION OF THE DRAWINGS

The various figures of the drawing depict illustrative and exemplary forms of the wound treatment device 10. Throughout the several views, identical reference characters represent similar or equivalent structures wherein:

FIG. 12A is a schematic drawing depicting functional relationships between several elements of the invention;

FIG. 12B is a schematic drawing depicting functional relationships between several elements of the invention;

FIG. 13A is a schematic drawing depicting functional relationships between several elements of the invention;

FIG. 13B is a schematic drawing depicting functional relationships between several elements of the invention;

FIG. 14A is a schematic drawing depicting functional relationships between several elements of the invention;

FIG. 14B is a schematic drawing depicting functional relationships between several elements of the invention;

FIG. 15 is a perspective view of an alternate version of the wound treatment device;

DETAILED DESCRIPTION

Figure 1:
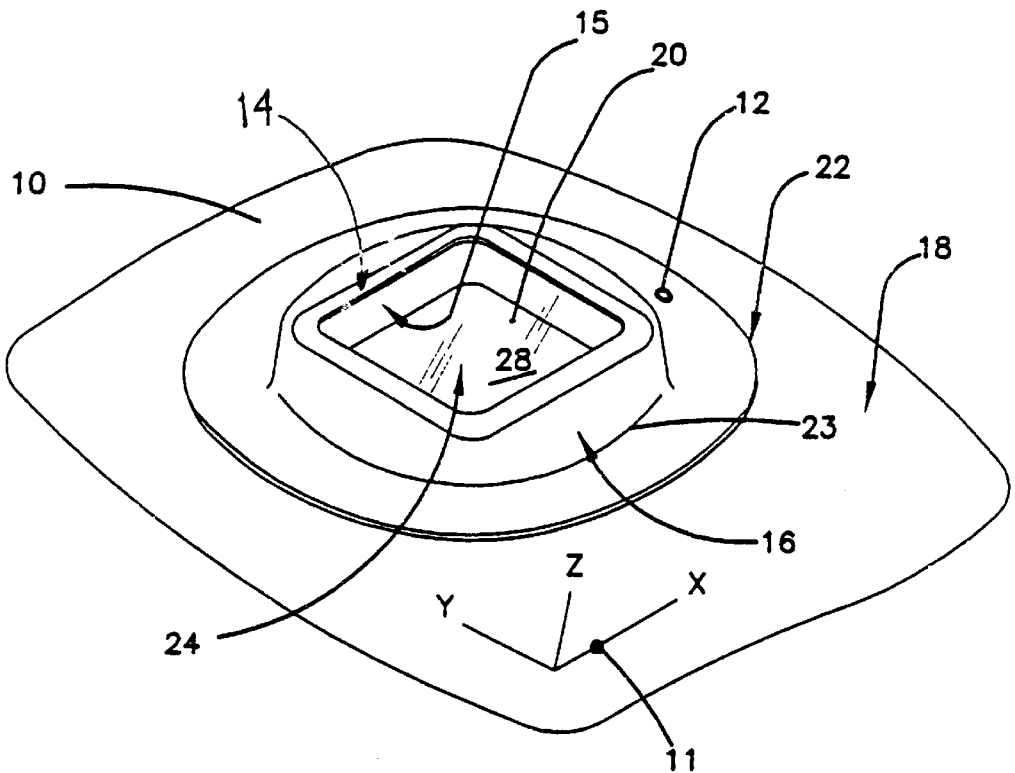
FIG. 1 is a perspective view of a first embodiment of the wound treatment device.

FIG. 1 is a perspective view of the wound treatment device 10 applied to a patient's skin surface 18. A coordinate system 11 is depicted on the patient's skin surface 18 and it defines X, Y and Z directions. The attachment portion 12 is formed as an planar rim or flange. This element is attached to the patient's skin with an adhesive and it lies in a first XY plane. In this first embodiment of the wound treatment device 10 the transition portion 16 is integrally formed with the attachment portion 12. The transition portion 16 rises vertically from the skin surface in the Z direction to connect to the wound treatment portion 14. In this embodiment the wound treatment portion 14 has a transparent planar wound cover 20 which allows one to see the wound treatment area 28. The wound cover 20 is supported above the first XY plane by a foam ring standoff 15. The planar wound cover 20 lies in a second XY plane that is vertically displaced along the Z-axis by the foam ring standoff 15 from the first XY plane. The wound cover 20 and foam ring standoff 15 together form the wound treatment portion 14. The region over the wound treatment area 28 is called the wound treatment volume 24.

In this figure the wound treatment device 10 has been applied to a patient's skin and is in a relaxed state. In this unstressed state one can see the outer periphery 22 of the attachment portion 12. The inner periphery 23 is shown by a crease in the structure where it connects to the transition portion 16.

Figure 2:
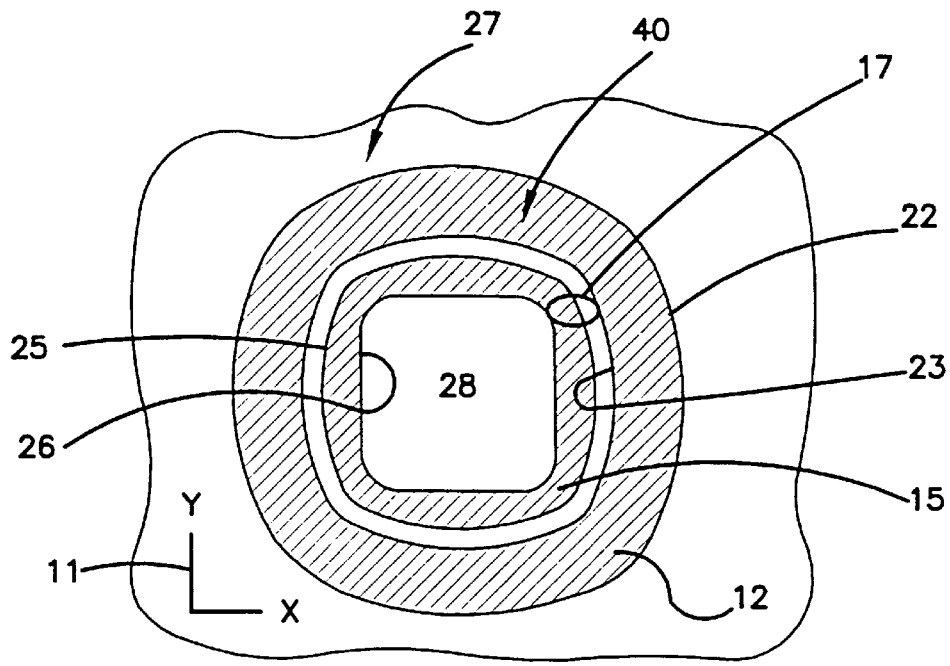
FIG. 2 is a schematic view of projected areas.
Figure 3:
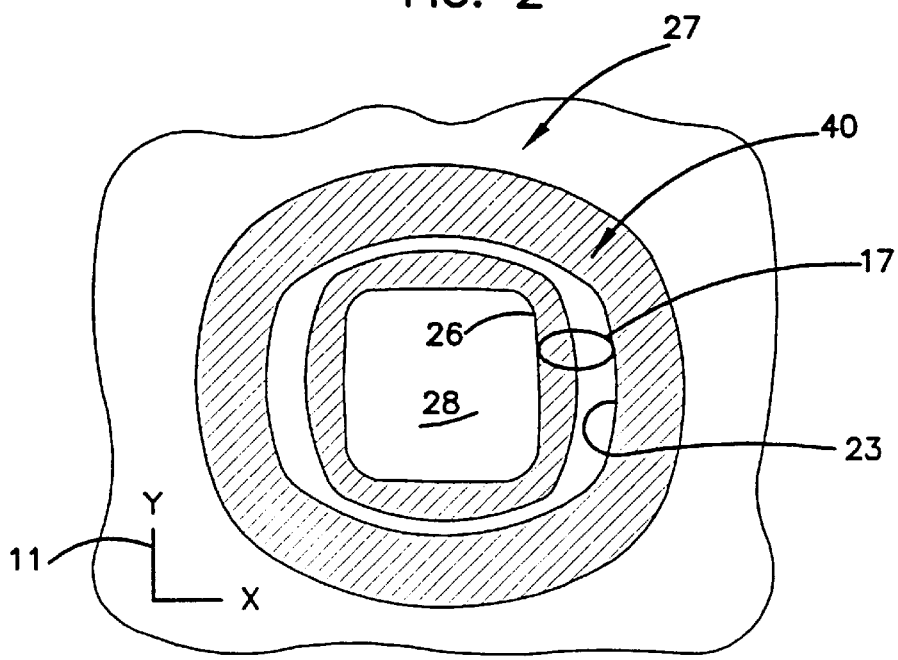
FIG. 3 is a schematic view of projected areas.

FIG. 2 and FIG. 3 should be considered together. Together they show the influence of patient motion on the wound treatment device 10. Both FIG. 2 and FIG. 3 are top views of the wound treatment device 10 of FIG. 1 with the various portions of the wound treatment device 10 projected onto the first XY plane.

In FIG. 2 the wound covering is shown in a relaxed and un-stretched state having a nominal total projected area 27. The projected wound treatment area 28 is shown at the center of the wound treatment device 10. The outline of the foam ring standoff 15 may be seen as the crosshatch area bounded by exterior perimeter 25 of the foam ring standoff 15, and the interior perimeter 26 of the foam ring standoff 15. The transition portion projected area 17 is shown in the figure bounded by the inner periphery 23 of the attachment portion 12, and the interior perimeter 26 of the foam ring standoff 15. The attachment portion projected area 40 is shown as the cross hatched area bounded by the outer periphery 22 and the inner periphery 23 of the attachment portion 12.

FIG. 3 shows the wound treatment device 10 stretched along the X-axis by patient motion. In comparison to FIG. 2 the overall or total projected area 27 of the wound treatment device 10 has increased. The attachment portion projected area 40 has increased slightly as the attachment portion moves with the underlying skin. The projected wound enclosure area 28 is essentially unchanged in area since in this embodiment the foam ring standoff 15 is free move against the skin. The largest percentage area change occurs in the transition portion projected area 17. As the wound treatment device 10 deforms in response to patient motion the transition portion is compliant and pays out material permitting the majority of the total projected area 27 increase to be accommodated primarily by the transition portion projected area 17.

Figure 4:
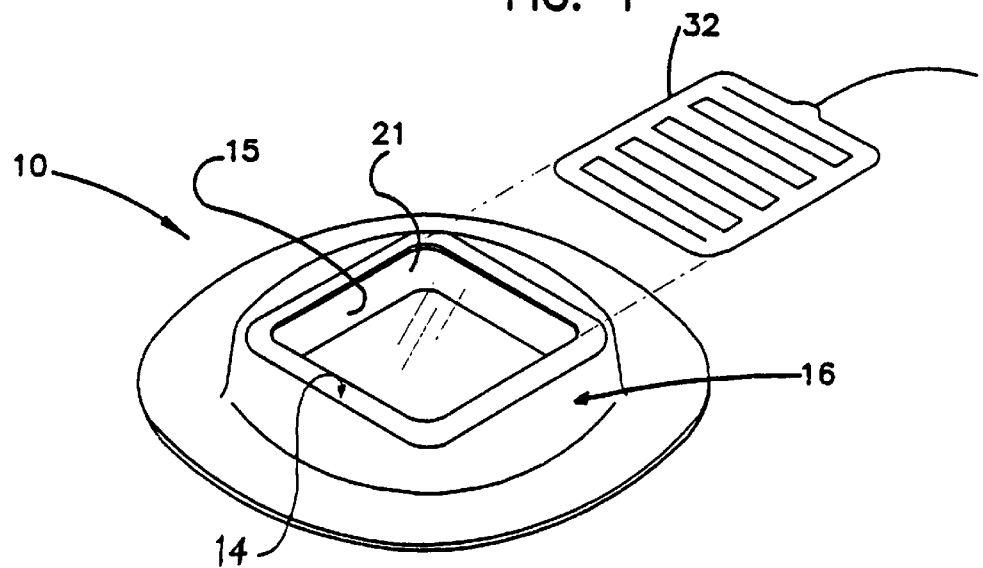
FIG. 4 is a perspective view of a detachable heater in combination with a first embodiment of the wound treatment device.

FIG. 4 shows a detachable heater 32 positioned for insertion into a pocket formed by pocket cover 21. Pocket cover 21 is bonded to the wound cover 20 and is sized to retain the heater 32. The foam ring standoff 15 and wound cover 20 serve to stabilize the shape of the wound treatment device while the transition portion accommodates patient motion. Consequently the heater is reliably and comfortably positioned above the wound surface. In general it is desirable to use a planar heater 32 which has a constant heat output per unit area. This form of heater results in a more uniform flux of radiant energy applied to the wound. And the amount of heat supplied to the wound area is largely independent of the height of the heater 32 above the wound surface.

Figure 5:
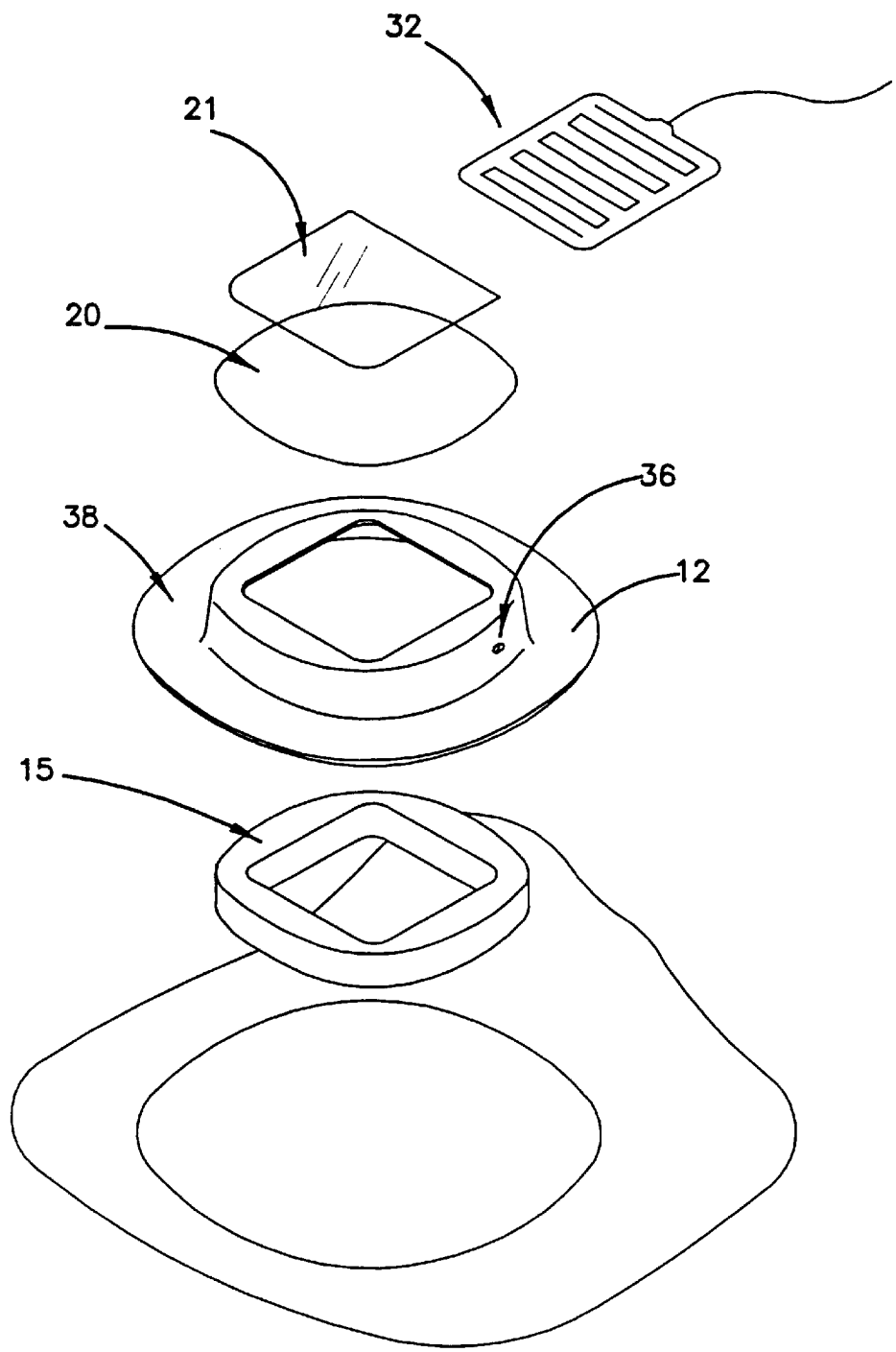
FIG. 5 is an exploded view of the first embodiment of the wound treatment device.

FIG. 5 is an exploded view of the first embodiment of the wound treatment device 10. The attachment portion 12 and transition portion membrane 36 are formed as a unitary composite shell 38. The composite shell may be vacuum formed from closed cell polyolefin foams such as Volara-6AS, which is a polyethylene material as sold by Illbruck, Inc., of Minneapolis, Minn., U.S.A. It should be apparent that many other materials may be substituted within the scope of the invention. The foam ring standoff 15 may be die cut from foam sheeting of a reticulated polyurethane foam. The absorbency of the foam as well as its mechanical properties can be tailored to the particular wound treatment application. For example, the foam standoff may be impregnated with a medicament such as an antibiotic; antifungal; or antimicrobial material. It may also be desirable to supply a deodorant material or nitric oxide releasing material from the foam standoff. The wound cover 20 and wound pocket 21 may be made from a thin film of polyethylene. In general, the composite shell should be sufficiently self supporting so that when the wound treatment device 10 is removed from its release liner the wound treatment portion 14 is held up or supported by the shaped flexion joint of the transition portion membrane 36, and some effort is required to evert the composite shell and turn it inside out. This behavior defines the self supporting feature which causes the foam ring standoff 15 to lie gently against the skin even when the wound treatment device 10 is upside down. For larger wound coverings it may be desirable to apply a tacky adhesive to the patient contact surface of the standoff.

Figure 6:
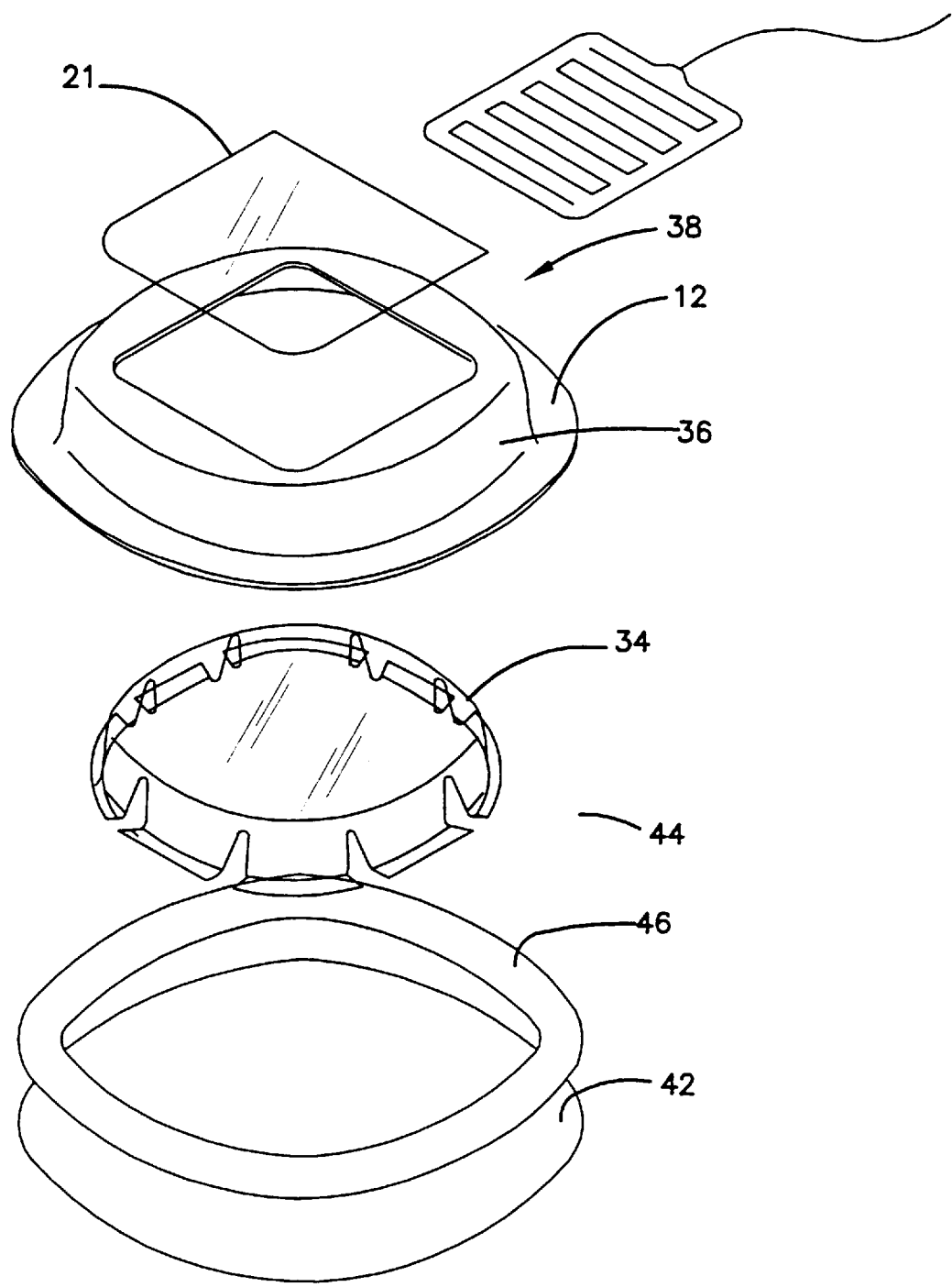
FIG. 6 is an exploded view of the second embodiment of the wound treatment device.

FIG. 6 is an exploded view of the second embodiment of the wound treatment device 10. The attachment portion 12 and transition portion membrane 36 are formed as a unitary composite shell 38. In this embodiment the wound treatment volume is formed by a serrated cup standoff 34. This member made be made from a more rigid polymeric material such as polyethylene or the like. The serrations typified by serration 44 permit the serrated cup to flex and accommodate patient motion. This embodiment shows a release liner 42 coupled to the attachment portion 12 of the composite shell 38 with an adhesive 46. In this embodiment the pocket cover 21 is bonded to the composite shell 38.

Figure 7:
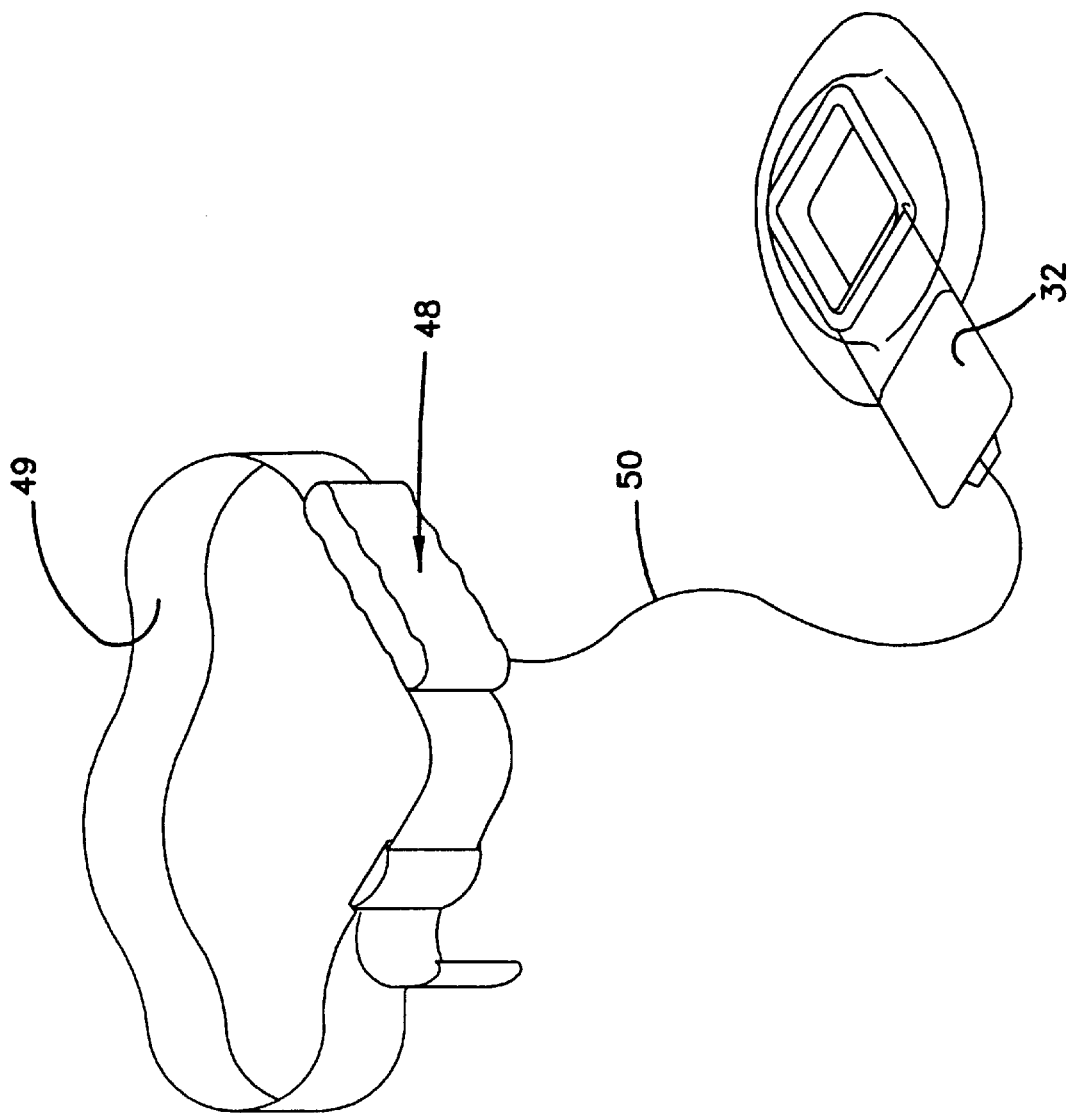
FIG. 7 is a perspective view of a heater system.

FIG. 7 depicts a power supply to permit the ambulatory use of the heated versions of the wound treatment device. A collection of battery cells may be wired together to form the power supply 48 which may be conveniently attached to a belt 49. A suitable cable 50 may be used to conduct power to the heater 32. In many instances it may be desirable to cut off power to the heater if the wound treatment device is collapsed against the wound to prevent overheating of the wound surface.

Figure 8:
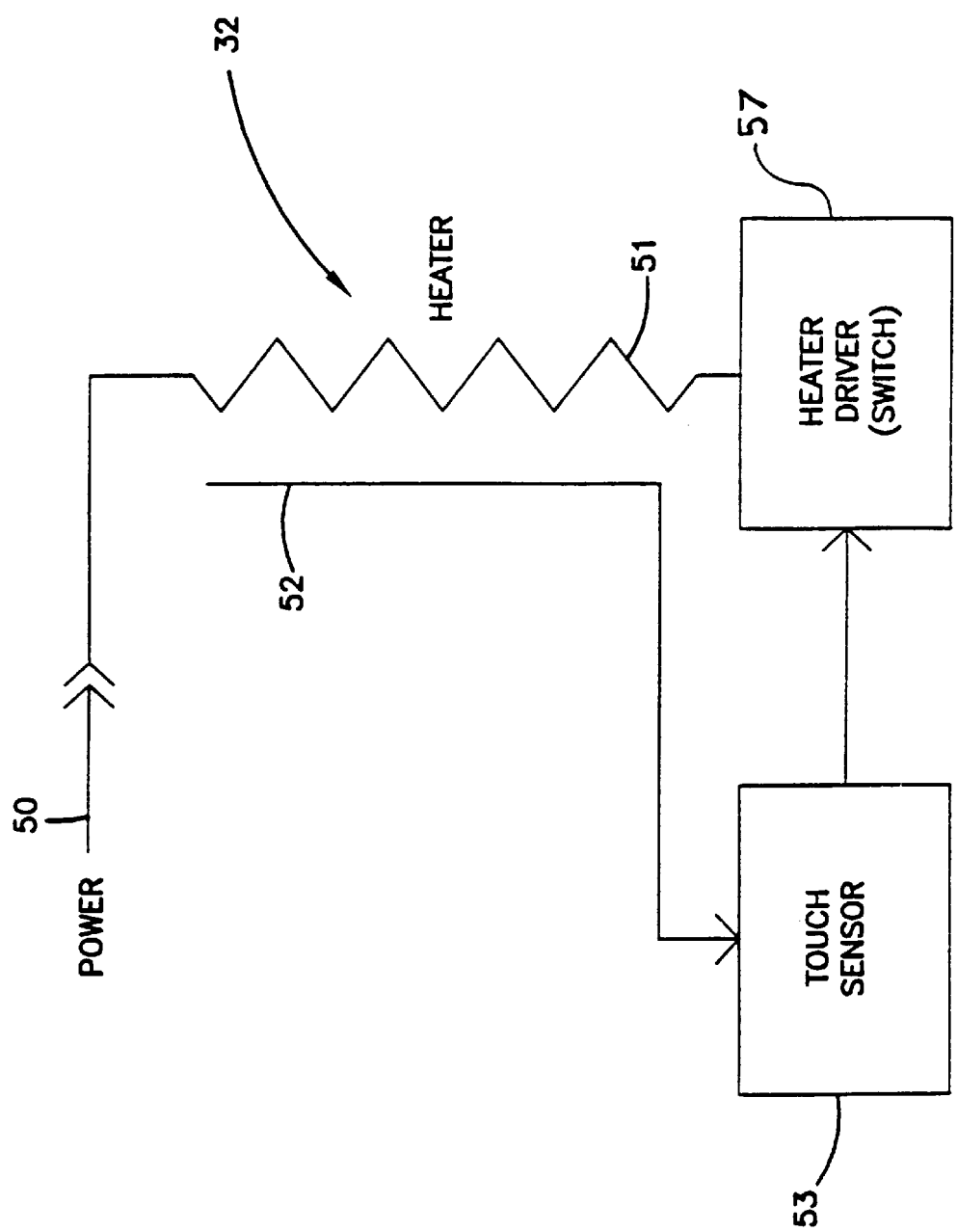
FIG. 8 is an electrical schematic of a pressure sensitive switch for a heater system.

FIG. 8 shows a schematic representation of a touch switch which may be incorporated directly into the detachable heater 32. The heater 32 includes a continuous resistive heating coil 51. A conductive membrane 52 is arranged near the coil 51 so that it may "short out" segments or portions of the coil 51. In use, power to the coil is completely turned off by pressure applied to the entire touch sensor 53. FIG. 8 also discloses a heater driver control switch 57 that operates by periodically activating planar heater 32 for treatment of the wound treatment area with heat.

Figure 9B:
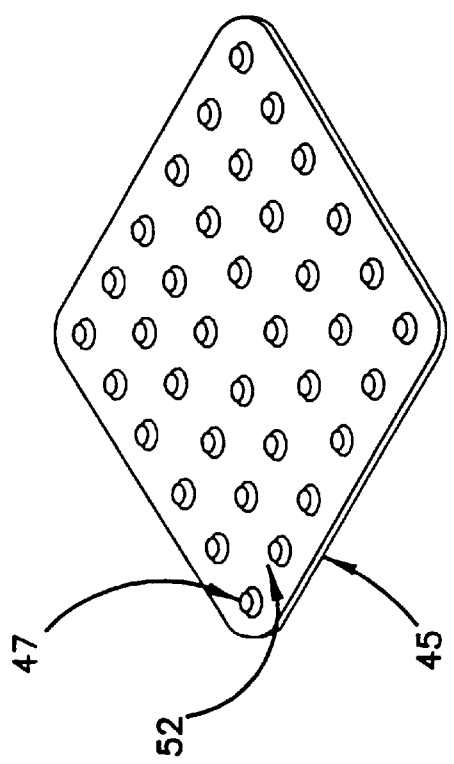
FIG. 9B is a view of a portion of the pressure sensitive switch.
Figure 9A:
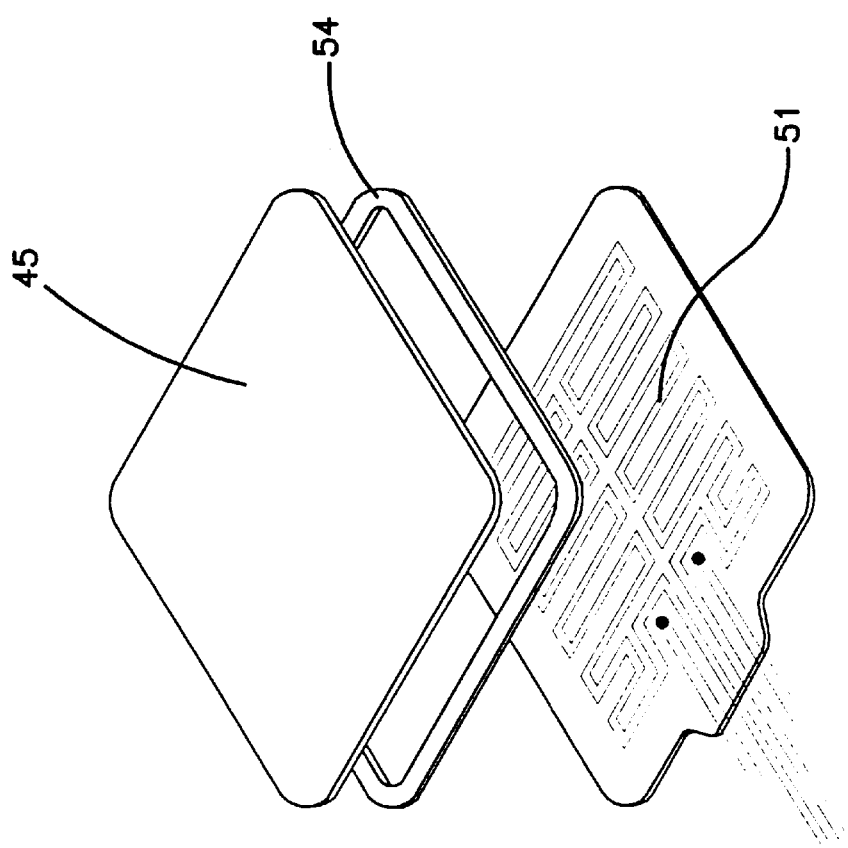
FIG. 9A is an exploded view of a pressure sensitive switch incorporated into a wound treatment device.

FIG. 9A shows an exploded version of the heater 32 which incorporates a touch switch of the type described schematically in FIG. 8. The switch cover 45 has a conductive membrane which is located over the conductive pattern of the heating coil 51. It is held in position with an adhesive band 54. FIG. 9B shows the underside of the switch cover 45 showing a number of discrete insulation bumps typified by bump 47 which serve to space and support the conductive membrane 52 above the heating coil pattern 51. Pressure supplied to the switch cover inactivates the heater coil 51.

Figure 10:
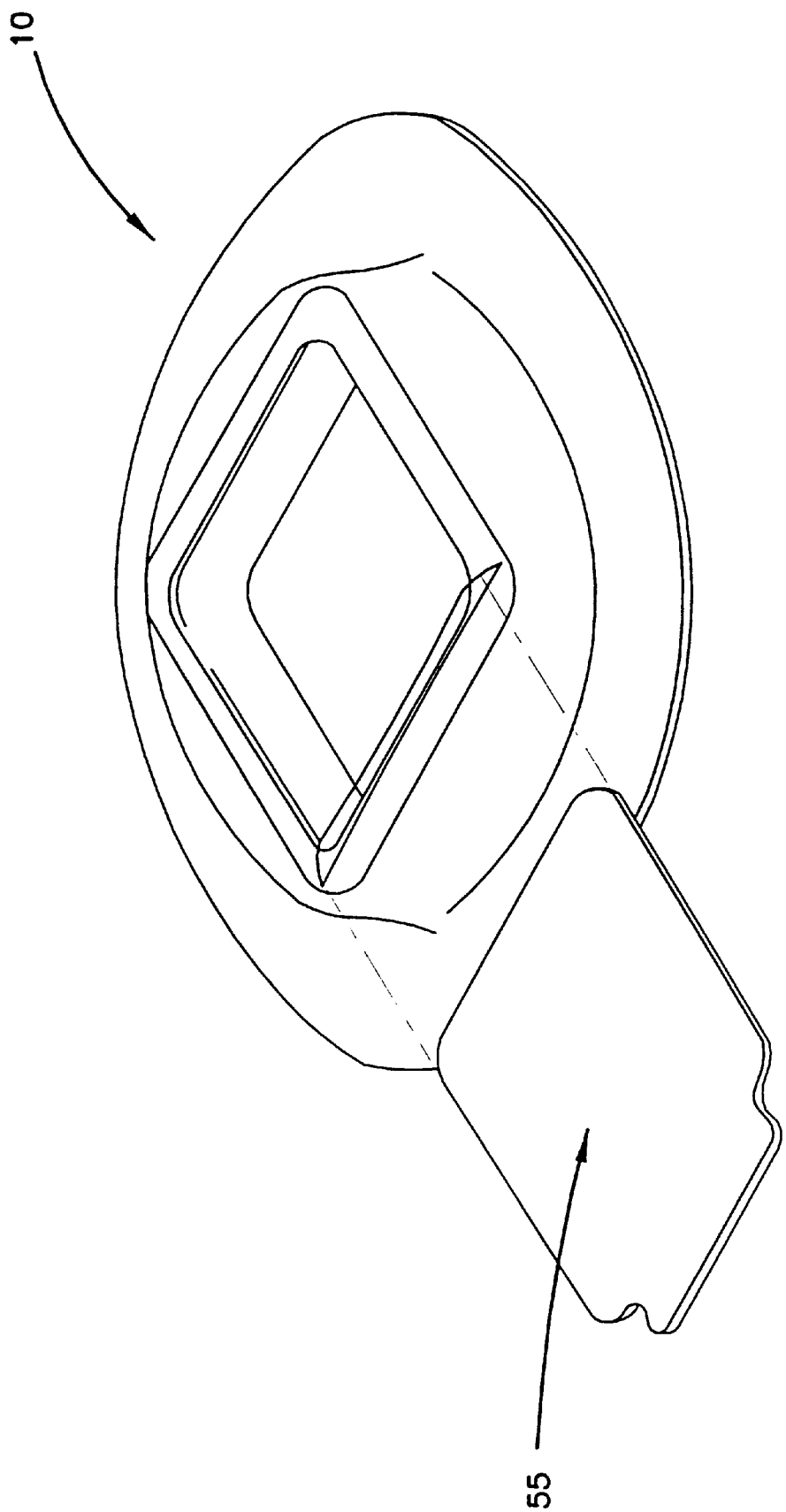
FIG. 10 is a perspective view of a passive heater embodiment of the wound treatment device.

FIG. 10 shows a an accessory device 55 or cover. This may take the form of a passive heater with a reflective surface facing the wound. The accessory device may also take the form of a mapping grid where a grid work of lines is positioned on a transparent card to permit tacking of the wound healing process.

FIG. 11A through FIG. 11D should be considered together. These drawings facilitate a description of connection structures of the invention and represent several alternative connection geometries. In general to accommodate patient motion the transition portion pays out stored material to increase the projected area of the transition portion. Each of these drawings represents a mechanical schematic cross section of a wound treatment device 10 in the XZ plane. In each figure the wound covering is in the relaxed state.

Figure 11A:
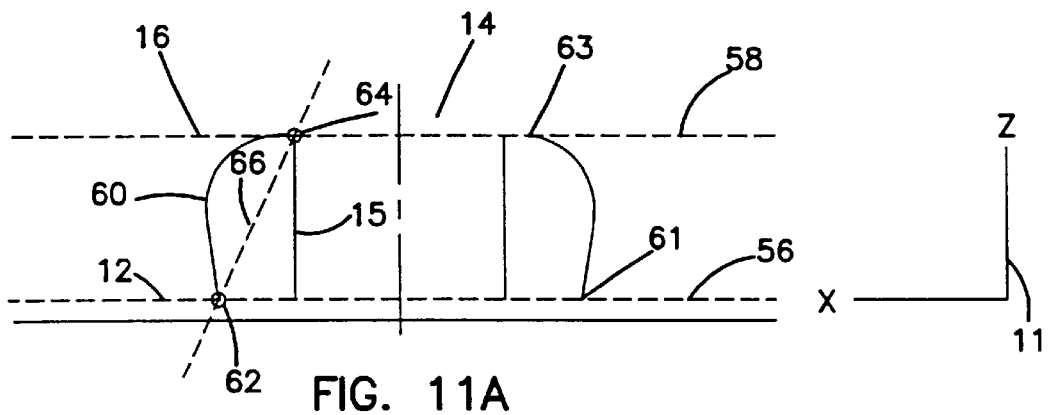
FIG. 11A is a schematic drawing depicting an alternate geometry for the transition portion.

FIG. 11A shows a schematic view of a ring standoff 15 extending from a first plane 56 to a second plane 58. The transition portion 16 has a transition portion membrane 60 which is coupled to the attachment portion 12 by a first flexible connection 62 formed at the intersection of the attachment portion 12 and the transition portion 16. The transition portion membrane 60 is connected to the treatment portion at a second flexible connection 64 which is formed at the intersection of the transition portion 16 and the wound treatment portion 14. The wound treatment portion 14 is generally a cylindrical cup shaped structure defining a wound treatment area on the patient skin surface. The minimum interconnection distance 66 is depicted as a dashed line extending from the first flexible connection 62 to the second flexible connection 64. The length of this minimum interconnection distance 66 can be used to characterize the "length" of the transition portion membrane 60. For many embodiments of the invention the length of the transition portion 16 between the first flexible connection 62 and the second flexible connection 64 is greater than the length of the straight line drawn between these points. This relationship is true for many embodiments of the wound treatment device when they are in the relaxed or unstressed position. It should be noted that the vertical distance between the first plane 56 and the second plane 58 represents a minimum value for the minimum interconnection distance 66. In the XY plane the first flexible connection 62 forms a first perimeter 61 and a second perimeter 63. In the embodiment depicted in FIG. 11A the first perimeter 61 is larger than the second perimeter 63.

Figure 11B:
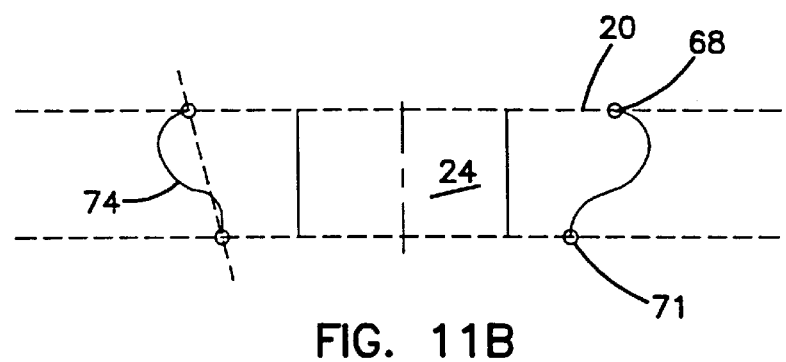
FIG. 11B is a schematic drawing depicting an alternate geometry for the transition portion.

FIG. 11B is a mechanical schematic diagram which represents a cross section of another embodiment of the wound treatment device 10 with an alternate connection geometry. In this drawing the wound cover 20 extends radially beyond the wound treatment volume 24 so that the second perimeter 68 is greater than the first perimeter 71. This generates a reflex transition portion 74 construction which may be adopted to increase the "length" and amount of material in the reflex transition portion 74.

Figure 11C:
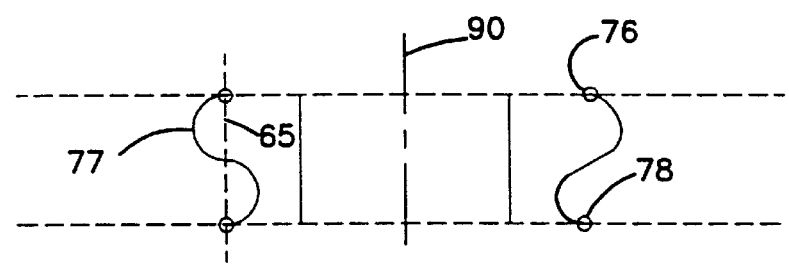
FIG. 11C is a schematic drawing depicting an alternate geometry for the transition portion.

FIG. 11C shows a construction where the first perimeter 76 and the second perimeter 78 have approximately the same value and are both concentric with the axis 90. This construction can produce an undulated transition portion 77. Once again the length of the undulated transition portion 77 exceeds the length of the line 65 between the first perimeter 76 and the second perimeter 78.

Figure 11D:
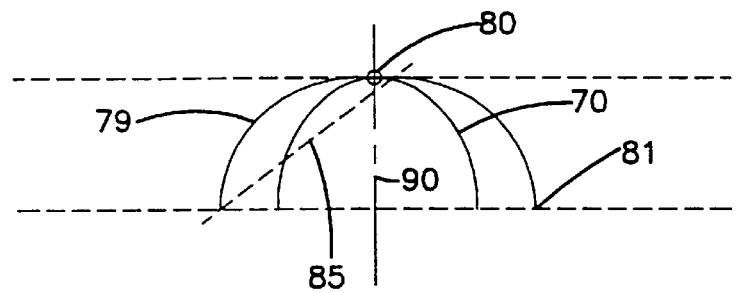
FIG. 11D is a schematic drawing depicting an alternate geometry for the transition portion.

FIG. 11D shows a hemispheric shell 70 as the wound treatment portion 14. In this embodiment the second perimeter 80 is a single attachment point generally concentric with the axis 90. In this embodiment the first perimeter 81 has a length which greatly exceeds the second perimeter 80 length. This construction forms a hemispheric transition portion 79 which has a length which exceeds the linear distance between the second perimeter 80 and the first perimeter 81 along the line 85.

Although the various geometries vary in detail it is preferred to form the transition portion from a resilient material which is generally self-supporting, yet sufficiently flexible so that it acts as a compliant hinge mechanism. This flexibility prevents the transfer of shearing force from the wound treatment portion 14 to the attachment portion 12 of the wound treatment device 10 and visa versa. With the geometries set forth in FIG. 11A through FIG. 11D the transition portion of the wound treatment device 10 forms a shaped flexion joint or formed expansion joint which stores "material" in a pleat convolution or bellows or the like. This type of structure provides a means for expanding the size of the transition portion to minimize the transfer of forces from the attachment portion 12 to the wound treatment portion 14.

FIG. 12A through FIG. 14B should be considered together. In these embodiments of the invention the standoff structure reduces in height to result in the increased transition portion area during the stretching of the wound treatment device.

FIG. 12A shows a part of a wound treatment device having a foam ring standoff 15 which is shown in the unstressed or relaxed state. In this instance the transition portion projected area 17 is proportional to dimension 88. In FIG. 12B the wound treatment device has been stretched and the height of the foam ring standoff 15 is reduced in the Z direction which has increased the transition portion projected area as represented by dimension 91.

FIG. 13A shows a part of a wound treatment device having a serrated cup standoff 34 which is shown in the unstressed or relaxed state. In this instance the transition portion projected area 17 is proportional to dimension 98. In FIG. 13B the wound treatment device has been stretched and the height of the serrated cup standoff 34 is reduced in the Z direction. The serrated wall sections splay out to permit the height reduction which has increased the transition portion projected area as represented by dimension 99.

FIG. 14A shows a part of a wound treatment device having a foam ring standoff 15 which is shown in the unstressed or relaxed state. However in this construction the attachment portion 12 and transition portion membrane 96 lie entirely in the first plane 56. In this instance the transition portion projected area 17 is proportional to dimension 94. In FIG. 14B the wound treatment device has been stretched and the height of the foam ring standoff 15 is reduced in the Z direction. This height reduction which has increased the transition portion projected area is represented by dimension 92.

FIG. 15 shows a version of the wound treatment device 10 which includes a dome shaped or hemispheric wound cover 19. At least a portion of this device lies in the second XY plane 58.

Figure 16:
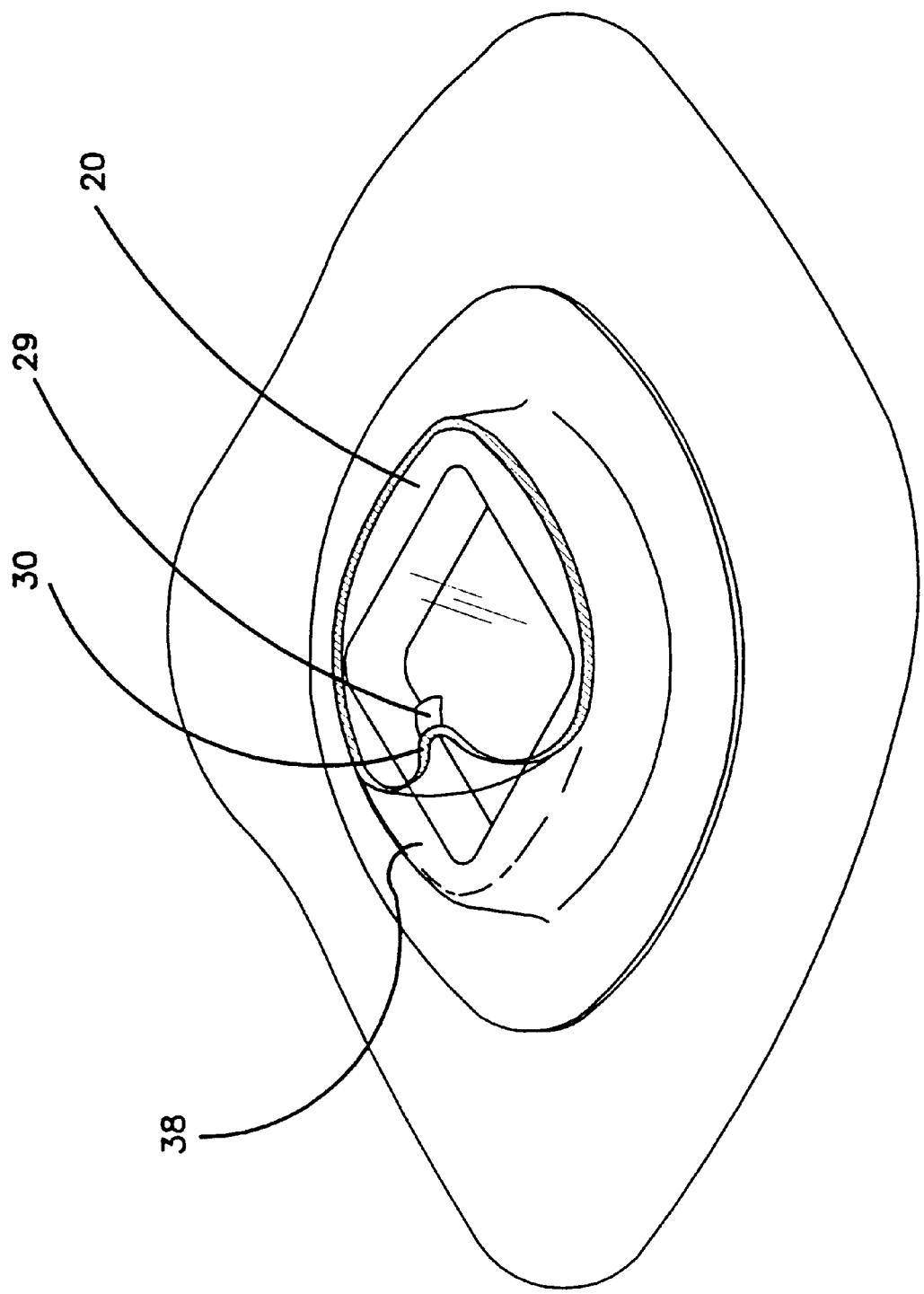
FIG. 16 is a perspective view of an alternate version of the wound treatment device.

FIG. 16 shows a version of the wound treatment device 10 which includes a releasable and resealable wound cover 20. To facilitate access to the wound the wound cover 20 may have a tab 29 located at the periphery of the wound cover 20. In general a reusable adhesive 30 may be applied to the periphery of the wound cover 20 as well to allow the cover to be releasable attached to the standoff 15 structure or composite shell 38.

Figure 17A:
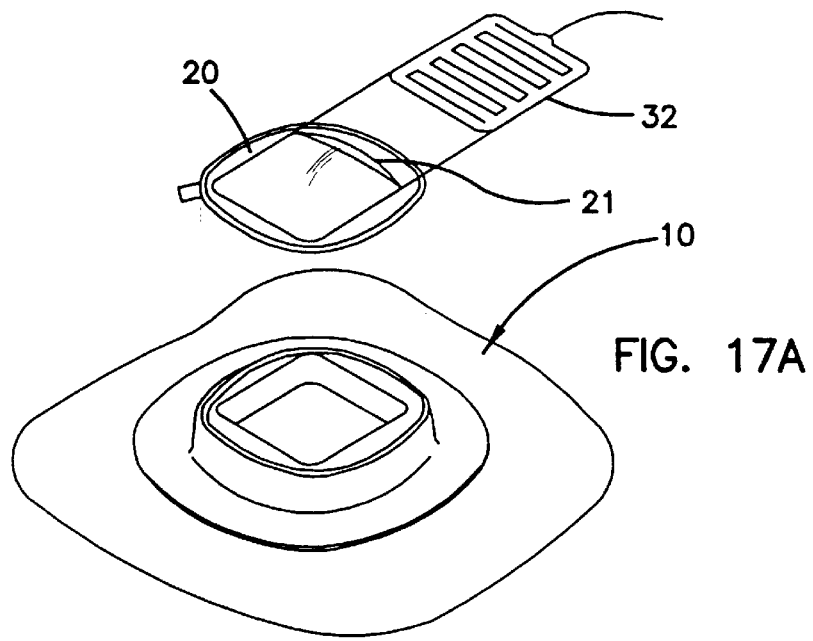
FIG. 17A is a perspective view of an alternate version of the wound treatment device with a heater.

FIG. 17A shows a releasable wound cover incorporating a heater pocket cover 21. In use the resealable wound cover 20 and pocket cover 21 forms a space for the heater 32.

Figure 17B:
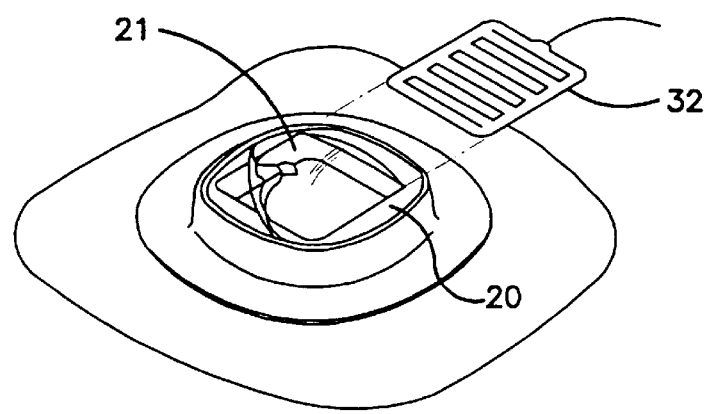
FIG. 17B is a perspective view of an alternate version of the wound treatment device with a heater.

FIG. 17B shows that one advantage of the resealable and removable construction is that the opening for the heater may be shifted without removing or repositioning the wound treatment device 10.

Figure 17C:
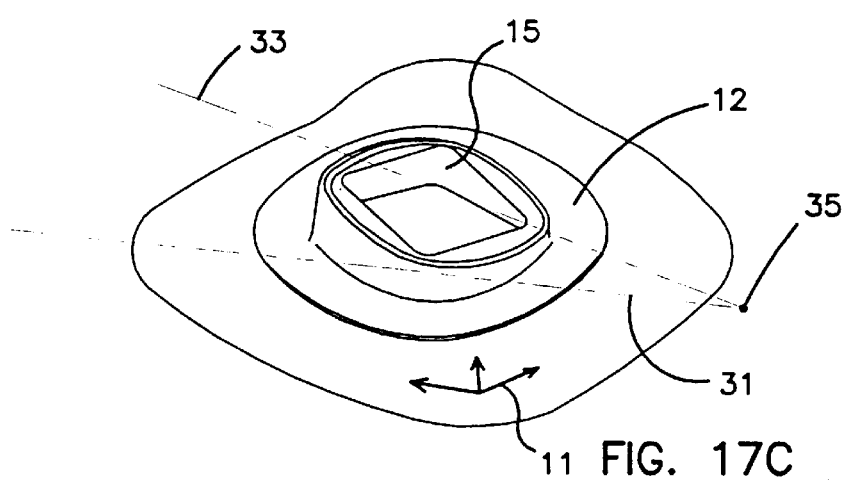
FIG. 17C is a perspective view of an alternate version of the wound treatment device.

FIG. 17C shows a wedge shaped wound treatment device 10. A line 31 in the XY plane 11 of the attachment portion 12 intersects with a line 33 which lies across the top of the standoff 15. These tow lines may meet a point 35 in space as seen in the drawing.

Figure 18:
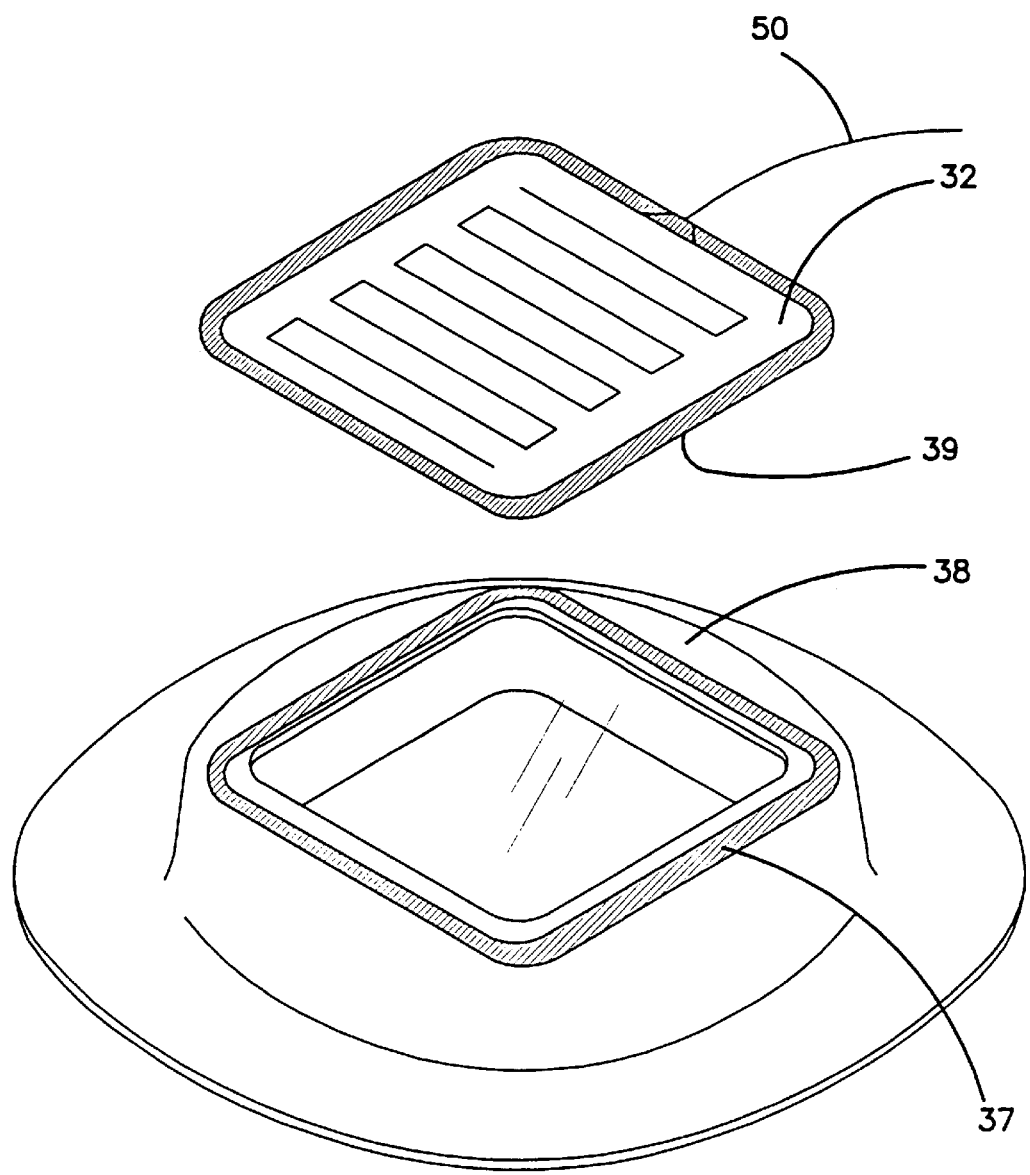
FIG. 18 is a perspective view of an alternate version of the wound treatment device with a heater.

FIG. 18 shows a an alternate method of attaching the planar heater 32 to the wound cover 20. In this embodiment the heater has a hook or loop material 37 attached to the edge of the heater 32 and the complimentary loop or hook material 39 is attached to the composite shell 38. In this embodiment the wound cover need not be accessible to reorient the heater 32. It should be appreciated that an adhesive may be used to attach the heater as well.

Figure 19A:
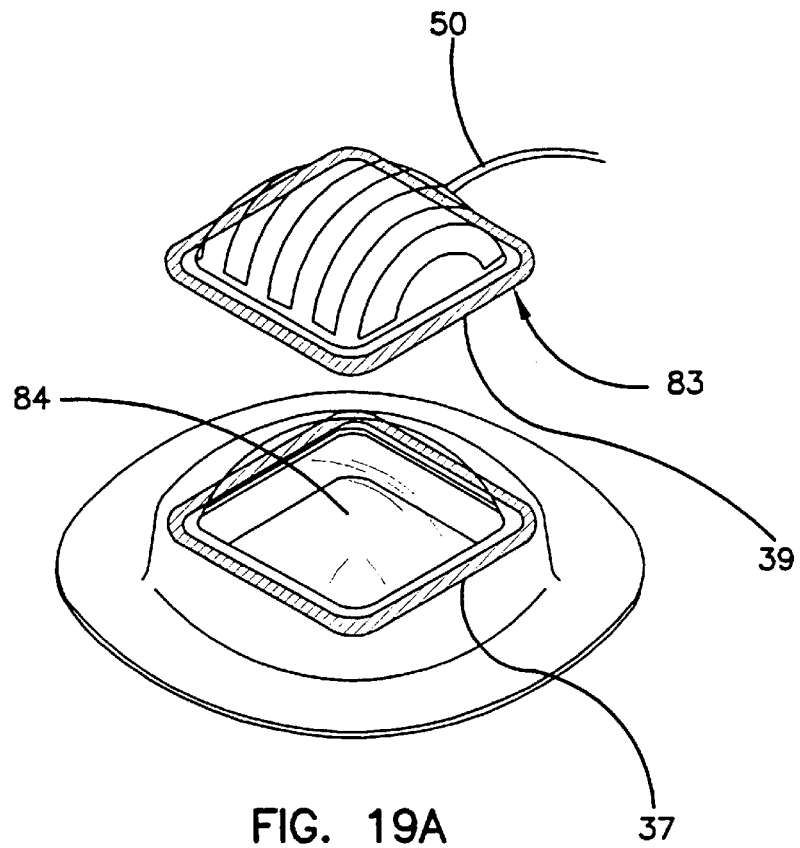
FIG. 19A is a perspective view of an alternate version of the wound treatment device with a heater.

FIG. 19A is a perspective view of an alternate version of the wound treatment device with a heater. It this embodiment the heater 83 is dome shaped to conform to the shape of the wound cover 84. complimentary loop and hook material 37 and 39 may be used for releasable attachment to the wound treatment device.

Figure 19B:
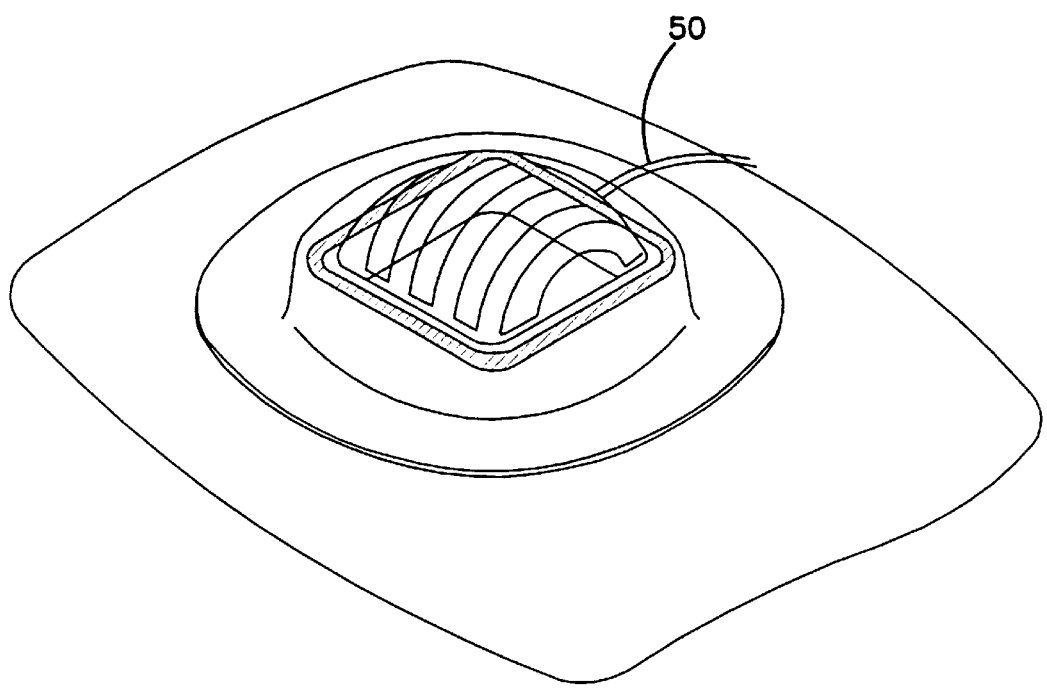
FIG. 19B is a perspective view of an alternate version of the wound treatment device with a heater.

FIG. 19B is a perspective view of an alternate version of the wound treatment device with a heater attached to the wound treatment device with an adhesive or the like. In this embodiment a resistive heater grid is formed in the cover to generate heat in response to electrical energy applied trough leads 50.

Figure 20A:
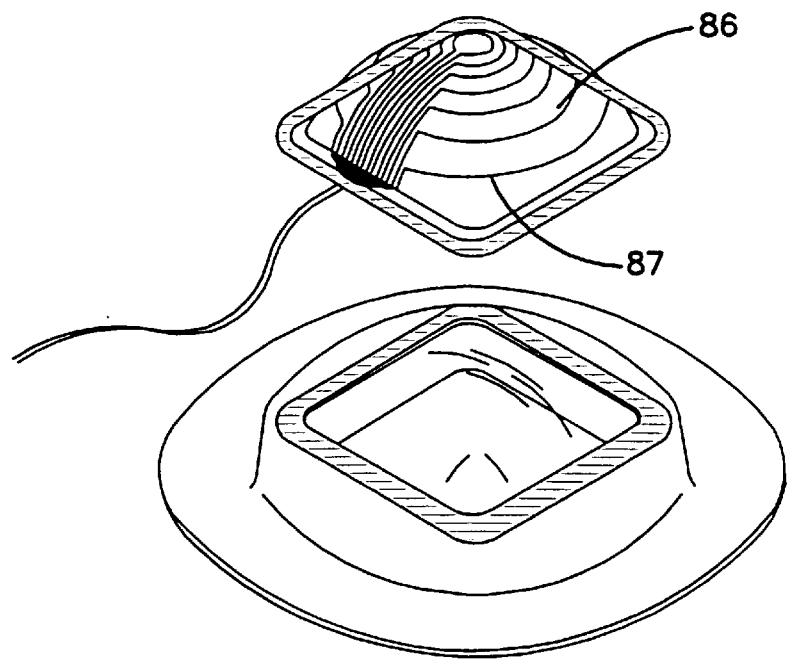
FIG. 20A is a perspective view of an alternate version of the wound treatment device with a heater.

FIG. 20A is a perspective view of an alternate version of the wound treatment device with a dome shaped heater 86. In this embodiment the heater 86 has a collection of independent parallel connected resistive loops typified by loop 87. In use the resistance of the loop is selected to ensure that the radiated heat is uniform as measured at the wound surface.

Figure 20B:
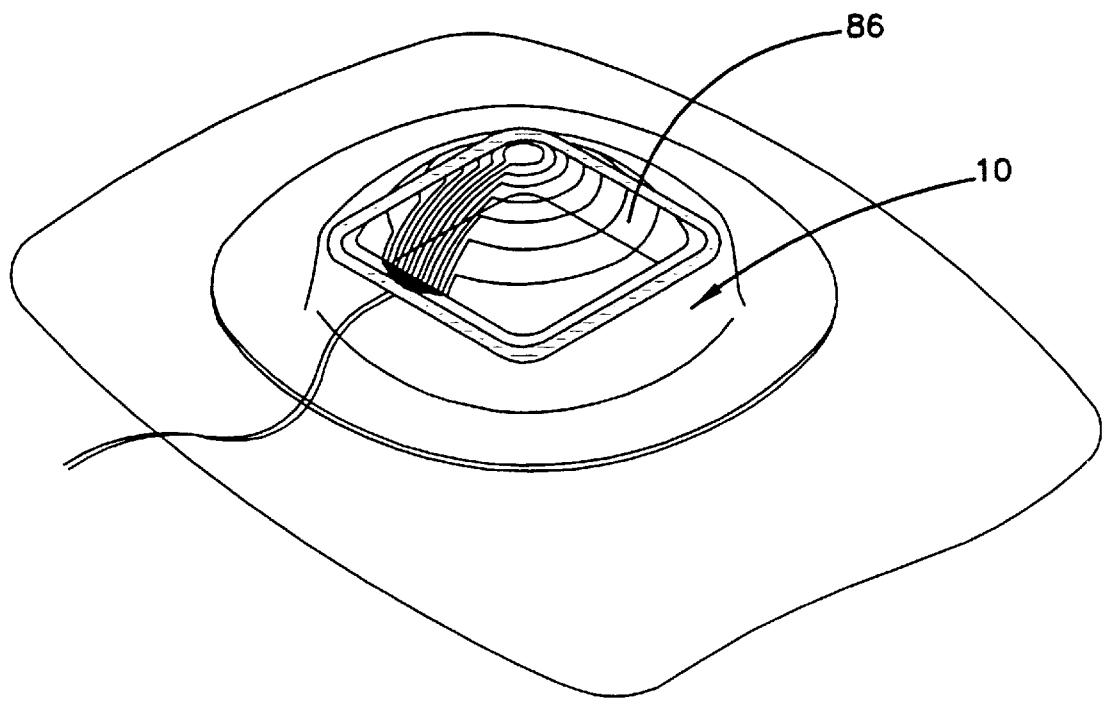
FIG. 20B is a perspective view of an alternate version of the wound treatment device with a heater.

FIG. 20B is a perspective view of an alternate version of the wound treatment device with a dome shaped heater 86 attached to the wound treatment device 10.

Figure 21A:
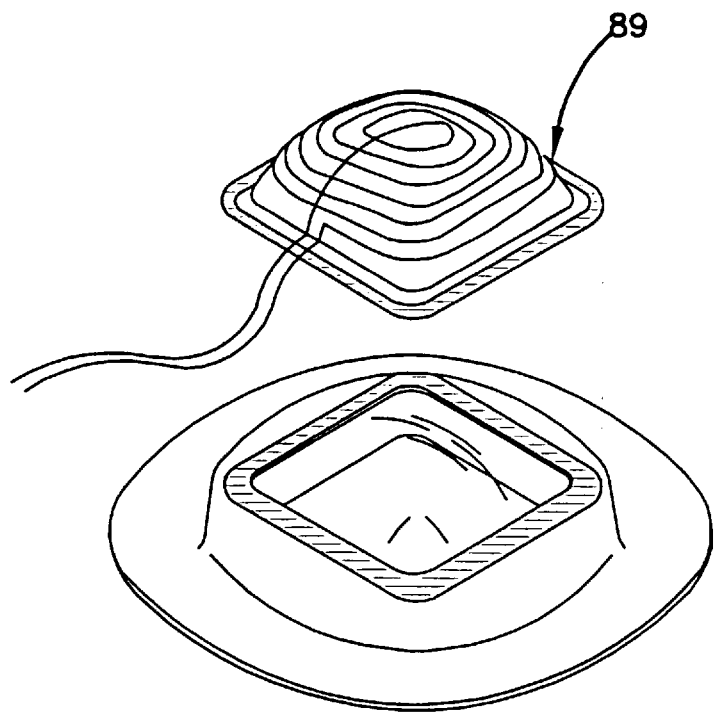
FIG. 21A is a perspective view of an alternate version of the wound treatment device with a heater.

FIG. 21A is a perspective view of an alternate version of the wound treatment device with a dome shaped heater 89. In this embodiment a heater wire is coiled to provide the heater element.

Figure 21B:
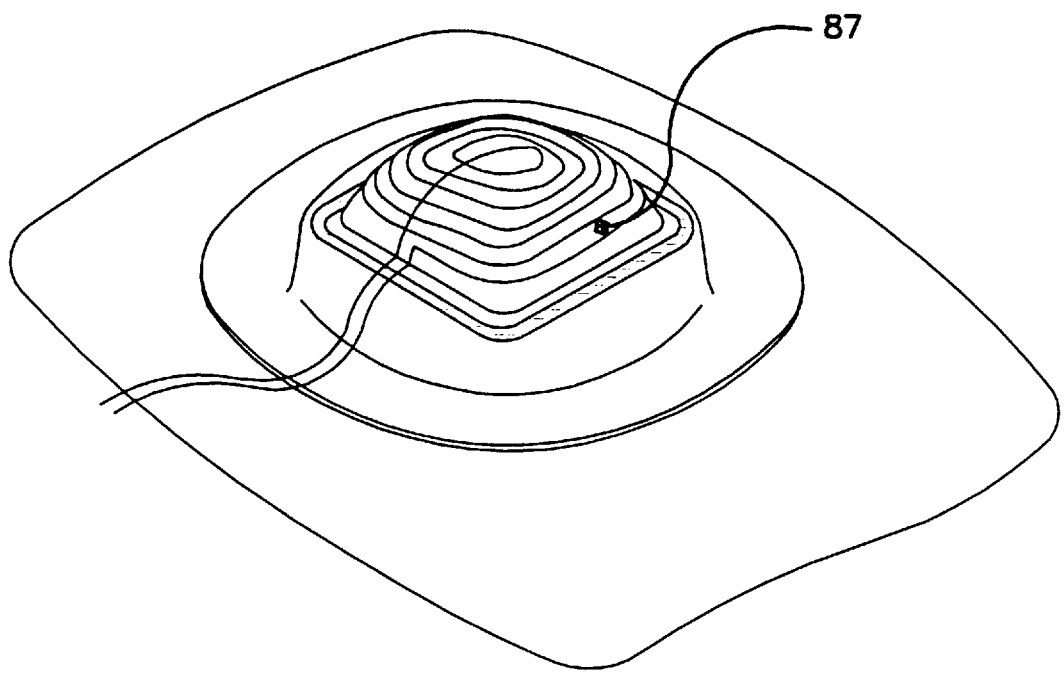
FIG. 21B is a perspective view of an alternate version of the wound treatment device with a heater.

FIG. 21B is a perspective view of an alternate version of the wound treatment device with a dome shaped heater 89. In use the coil spacing indicated by dimension 87 can be adjusted to provide uniform heating of the wound area.

Figure 22A:
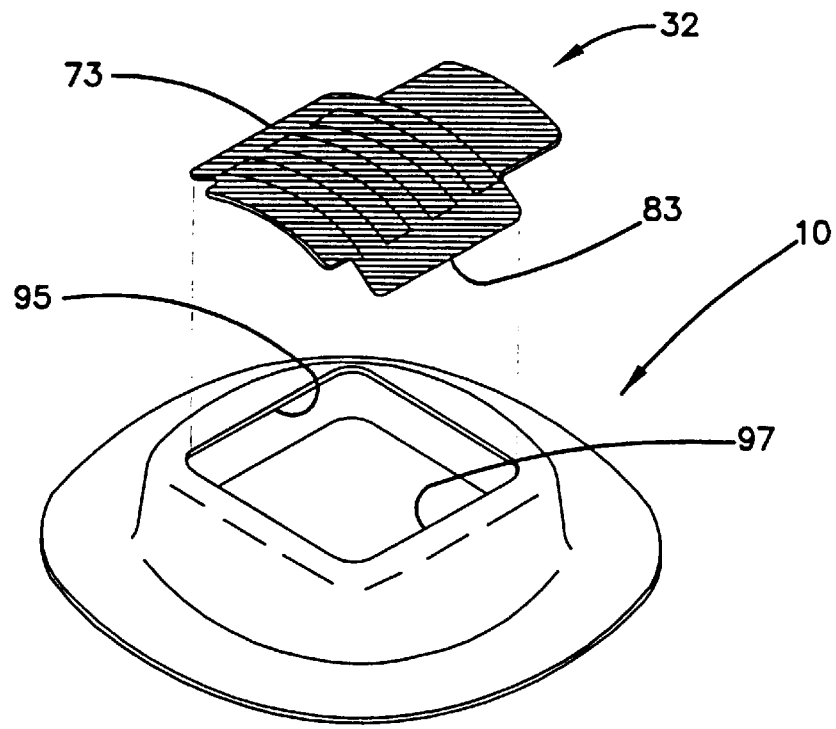
FIG. 22A is a perspective view of an alternate version of the wound treatment device with a heater.

FIG. 22A is a perspective view of a wound treatment device 10 having two complimentary pockets shown as pocket 97 and pocket 95 which cooperate with tab 83 and tab 75 formed on the heater 32.

Figure 22B:
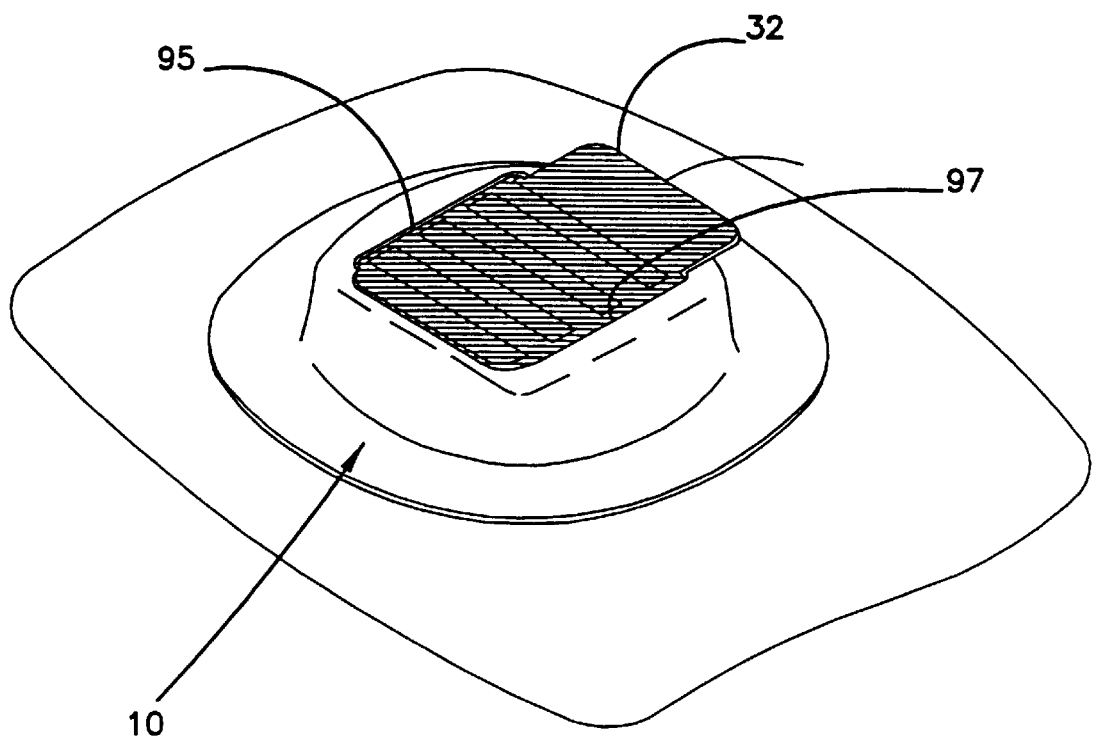
FIG. 22B is a perspective view of an alternate version of the wound treatment device with a heater.

FIG. 22B is a perspective view which shows tab 75 and tab 83 inserted into the complimentary pockets 95 and pocket 97 to position and retain a planar heater structure.

Having thus described the invention it should be apparent that numerous changes may be made without departing from the scope of the invention as defined by the claims.

What is claimed is:

1. A wound treatment device (10) having an attachment portion (12) for releasable attachment to a patient's skin surface (18) proximate a wound treatment area (28), said attachment portion (12) defining a first plane for placement near the wound treatment area, wherein said wound treatment device (10) improvement comprises:

a resilient standoff (15), within said attachment portion (12), extending from said first plane to a second plane, said standoff for maintaining the second plane in a non-contact position with respect to the wound treatment area (28);

a wound treatment portion (14) proximate said second plane, defining a non-contact wound treatment volume (24); and a compliant transition portion (16) extending from said attachment portion (12) to treatment portion (14) for coupling said attachment portion (12) to said treatment portion (14), said transition portion (16) including a membrane (36) connected to said attachment portion (12) proximate said first plane and connected to said standoff (15) at said second plane.

2. The wound treatment device of claim 1 wherein said resilient standoff (15) terminates at said second plane and said second plane is parallel to said first plane.

3. The wound treatment device of claim 1 wherein said transition portion (16) comprises:

a shaped flexion joint membrane (60) coupled to said attachment portion (12) at a first connection (62), said first connection (62) proximate said first plane, and connected to said flexible standoff (15) at a second connection (64), said second connection (64) proximate said second plane;

the linear distance between said first connection and said second connection defining a minimum interconnection distance (66);

said shaped flexion joint membrane (60) extending between said first connection (62) and said second connection (64), and having a curvilinear length which exceeds said minimum interconnection distance when said wound treatment device (10) is in said relaxed state.

4. The wound treatment device of claim 1 wherein said transition portion (16) comprises:

a shaped flexion joint membrane (60) coupled to said attachment portion at a first connection (62), said first connection (62) proximate said first plane, and coupled to said resilient standoff (15) at a second connection (64), said second connection (64) proximate said second plane;

the linear distance between said first connection (62) and said second connection (64) defining a minimum interconnection distance (66);

said shaped flexion joint membrane (60) extending between said first connection and said second connection, and having a curvilinear length which exceeds said minimum interconnection distance.

5. The wound treatment device of claim 1 wherein said transition portion (16) comprises:

a substantially inelastic membrane connected to said resilient standoff (15) proximate said second plane, and connected to said attachment portion proximate said first plane.

6. The wound treatment device of claim 1 wherein said resilient standoff (15) comprises a polymeric foam ring having an interior wall and having an exterior wall, each of said walls extending from said first plane to said second plane and said treatment portion comprises a wound cover spanning at least the distance of said interior wall, forming a closed wound treatment volume.

7. The wound treatment device of claim 6, wherein said wound cover (20) is coupled to said treatment portion (14) by an adhesive.

8. The wound treatment device of claim 6, wherein said wound cover (20) is coupled to said treatment portion by a reusable adhesive whereby said wound cover (20) can be removed and repositioned on said foam ring thereby permitting access to said wound area.

9. The wound treatment device of claim 6, wherein said wound cover (20) is coupled to said treatment portion (14) by a reusable adhesive (30) said wound cover (20) including a grip tab (29) for facilitating removal and repositioning of said wound cover (20) on said foam ring, thereby permitting access to said wound area.

10. The wound treatment device of claim 6, wherein said wound cover (20) is releasably coupled to said treatment portion (14) by a hook and loop material whereby said wound cover (20) can be removed and repositioned on said foam ring thereby permitting access to said wound area (28).

11. The wound treatment device of claim 6, wherein said polymeric foam ring is made from polyurethane.

12. The wound treatment device of claim 6, wherein said polymeric foam ring is made from a reticulated polyurethane.

13. The wound treatment device of claim 6, wherein said polymeric foam ring is impregnated with a medicament for release into said wound treatment volume.

14. The wound treatment device of claim 13 wherein said medicament is an antimicrobial material.

15. The wound treatment device of claim 13, wherein said medicament releases nitric oxide.

16. The wound treatment device of claim 6, wherein said polymeric foam ring is impregnated with a medicament for release into said wound treatment volume by the application of heat to said wound treatment volume.

17. The wound treatment device of claim 6, wherein said polymeric foam ring is impregnated with a deodorant.

18. The wound treatment device of claim 1 wherein said resilient standoff (15) comprises a polymeric cup (34) having a wall and a unitary cover section lying at least partially in said second plane, said wall extending from said first plane to said second plane, said polymeric cup (34) defining and enclosing a wound treatment volume.

19. The wound treatment device of claim 18, wherein said polymeric cup (34) wall is serrated.

20. A wound treatment device (10) having an attachment portion (12) for contacting and releasably attaching to a patient's skin surface (18) proximate a wound treatment area (28), said attachment portion (12) defining a first plane for placement near the wound treatment area, wherein said wound treatment device (10) further comprises:
 a standoff (15), extending from said first plane to a second plane, having a hollow interior defining a wound treatment volume (24);
 a transition portion (16) connected to said attachment portion (12) at said first plane and connected to said standoff (15) at said second plane; and
 a heater (32) proximate said second plane of said standoff (15) over the wound treatment volume (24), said heater having an active area for radiating heat through the wound treatment volume (24) toward said first plane.

21. The wound treatment device of claim 20, wherein said heater (32) has a substantially planar surface with one or more resistive heating elements arranged to radiate heat into said wound treatment volume.

22. The wound treatment device of claim 20, wherein said heater (32) active area extends across at least the center of said first plane.

23. The wound treatment device of claim 20, wherein said heater (86) has a substantially dome shaped surface with one or more resistive heating elements arranged to radiate heat into said wound treatment volume.

24. The wound treatment device of claim 20, wherein the standoff (15) includes a polymeric foam ring, extending from said first plane to said second plane and including a hollow interior defining the wound treatment volume (24).

25. The wound treatment device of claim 28 wherein said heater (86) radiates heat substantially uniformly across said first plane.

26. The wound treatment device of claim 20, further comprising a wound cover portion (20) connected to said standoff (15), proximate said second plane.

27. The wound treatment device of claim 26, wherein said second plane is substantially parallel to said first plane, and said standoff (15) terminates at said second plane.

28. The wound treatment device of claim 26, wherein said wound cover (20) is openable and resealable and includes said heater (32) spanning said standoff.

29. The wound treatment device of claim 26, further comprising a pocket (21) formed proximate said wound cover (20) for receiving and retaining said heater (32) proximate said second plane.

30. The wound treatment device of claim 26, further comprising a hook and loop material proximate said wound cover (20) for receiving and retaining said heater (32) proximate said second plane.

31. The wound treatment device of claim 26, further comprising an adhesive material for coupling said wound cover (20) to said wound treatment device for receiving and retaining said heater (32) proximate said second plane.

32. The wound treatment device of claim 26, further comprising an adhesive material for releasably coupling said wound cover (20) to said wound treatment device (10).

33. The wound treatment device of claim 26, further comprising a hook and loop material proximate said treatment portion (14) for receiving and retaining said heater (32) proximate said second plane.

34. The wound treatment device of claim 26 further comprising an adhesive material proximate said periphery of said treatment portion (14) for receiving and retaining said heater (32) proximate said second plane.

35. The wound treatment device of claim 26 further comprising an adhesive material proximate said periphery of said treatment portion (14) for releasably receiving and retaining said heater (32) proximate said second plane.

36. The wound treatment device of claim 20 further comprising a switch (53) located on said wound treatment device (10) and coupled to said heater (32) for turning off said heater (32).

37. The wound treatment device of claim 20 further comprising a switch (52) located on said heater (32) for turning off said heater (32).

38. The wound treatment device of claim 20 further comprising a heater driver switch (57) coupled to said heater (32) for periodically activating said heater (32).

39. A wound treatment device (10) having an attachment portion (12) for releasable attachment to a patient's skin surface (18) proximate a wound treatment area (28), said attachment portion (12) defining a first plane for placement near the wound treatment area, wherein said wound treatment device (10) further comprises:
 a standoff (15) extending from said first plane to a second plane, said standoff (15) defining a wound treatment volume (24);
 a compliant transition portion (16) operably connected to said standoff (15) proximate said second plane and connected to said attachment portion (12) proximate said first plane; and
 a heat reflector (55) proximate said standoff (15) proximate said second plane for reflecting heat into said wound treatment volume (24).

40. The wound treatment device of claim 39, wherein said heat reflector (55) is releasably attachable to said standoff (15) forming a wound covering (20).

41. The wound treatment device of claim 39, further including a loop and hook material for attaching said heat reflector (55) to said standoff (15).

42. The wound treatment device of claim 39, further including an adhesive material for attaching said heat reflector (55) to said standoff (15).

43. The wound treatment device of claim 39, further comprising a wound cover (20) spanning said standoff (15) proximate said second plane, and including a pocket (21) for receiving said heat reflector (55).

44. The wound treatment device of claim 37, wherein said switch (52) comprises a switch membrane (45) positionable proximate said heater (32) for disconnecting sections of said heater (32).

45. The wound treatment device of claim 20, further comprising a power source (48) for operating said heater.

46. A method of making a wound treatment device comprising the steps of:

forming a unitary cup shaped member having an attachment portion and having a transition portion and having a wound treatment portion;

removing an area of said cup member to form a window zone;

attaching a wound cover to said window zone;

positioning and attaching a wound enclosure ring proximate said wound cover;

adhesively applying a release liner to said attachment portion.

* * * * *

UNITED STATES PATENT AND TRADEMARK OFFICE
CERTIFICATE OF CORRECTION

PATENT NO. : 6,013,097
DATED : January 11, 2000
INVENTOR(S) : Augustine et al

It is certified that error appears in the above-identified patent and that said Letters Patent is hereby corrected as shown below:

On the title page, third inventor, should read
-- [75] Donald E. Stapf, Minneapolis --
Assignee should read
-- [73] AUGUSTINE MEDICAL, INC., Eden Prairie, Minnesota --

Signed and Sealed this

Fifteenth Day of August, 2000

Attest:

Q. TODD DICKINSON

Attesting Officer

Director of Patents and Trademarks